United States Patent
Wang

[11] Patent Number: 5,858,988
[45] Date of Patent: *Jan. 12, 1999

[54] POLY-SUBSTITUTED-PHENYL-OLIGORIBO NUCLEOTIDES HAVING ENHANCED STABILITY AND MEMBRANE PERMEABILITY AND METHODS OF USE

[76] Inventor: Jui H. Wang, 5500 N. Bailey Ave., Amherst, N.Y. 14226

[*] Notice: The term of this patent shall not extend beyond the expiration date of Pat. No. 5,459,646.

[21] Appl. No.: 604,871

[22] Filed: Feb. 22, 1996

Related U.S. Application Data

[63] Continuation-in-part of Ser. No. 200,650, Feb. 23, 1994, Pat. No. 5,496,546, which is a continuation-in-part of Ser. No. 22,055, Feb. 24, 1993, abandoned.

[51] Int. Cl.⁶ ............... A61K 48/00; C12Q 1/68; C07H 21/01
[52] U.S. Cl. ............... 514/44; 135/6; 135/91.1; 135/375; 536/23.1
[58] Field of Search ............... 435/6, 375, 325; 536/23.1, 24.3, 24.31, 24.32, 24.5, 25.1; 514/44; 935/33, 34

[56] References Cited

U.S. PATENT DOCUMENTS

| | | | |
|---|---|---|---|
| 5,466,786 | 11/1995 | Buhr et al. | 536/26.26 |
| 5,496,546 | 3/1996 | Wang et al. | 424/78.36 |
| 5,514,577 | 5/1996 | Draper et al. | 435/238 |

FOREIGN PATENT DOCUMENTS 9220697  11/1992  WIPO ............... C07H 21/00

OTHER PUBLICATIONS

E. Lesnik et al. Biochem. 32: 7837–8 1993.
J Grzybowski et al. Nucl. Acids Res. 21(8): 1705–12 1993.
Steward, David L., et al., "Influence of 2'O–acetylation on the antiviral activity of polyribonucleotides", *Biochim. Biophys. Acta*, 262, 227–232, (1972).

Chuan, Hua, et al., "3'O–(5–Fluro–2,4–dinitrphenyl)ADP Ether and ATP Ether", *The Journal of Biological Chemistry*, vol. 263, No. 26, 13003–13006, Sep. 15, 1988..
Kang Insug, et al., "Design of Structure–based Reverse Transcriptase Inhibitors", *The Journal of Biological Chemistry*, vol. 269, No. 16, 12024–12031, Apr. 22, 1994.
Steward, et al., Chem. Ab., 77 77: 1242G.
William, Chem. Ab., 87 (23) 177597, (1977).
Chem. Ab., 83:158731 (1975).

*Primary Examiner*—John L. LeGuyader
*Attorney, Agent, or Firm*—Fliesler, Dubb, Meyer & Lovejoy

[57] ABSTRACT

In accordance with the present invention, antisense oligonucleotides are provided with enhanced membrane permeability and stability. This is accomplished in accordance with the invention through conjugating oligoribonucleotides with a hydrophobic carrier agent at the 2'-O position of the oligonucleotides. The hydrophobic carrier agent comprises a compound of the following general structure:

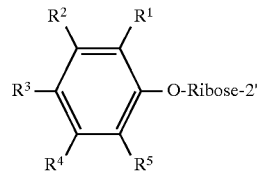

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$. In such embodiment, it will be appreciated that when $R^2$, $R^4$, and $R^5$ are H, the compound is DNP and when $R^4$ is F, the compound is FDNP.

63 Claims, 8 Drawing Sheets

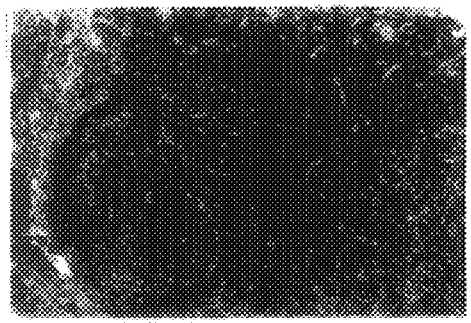
FIG. 8A1
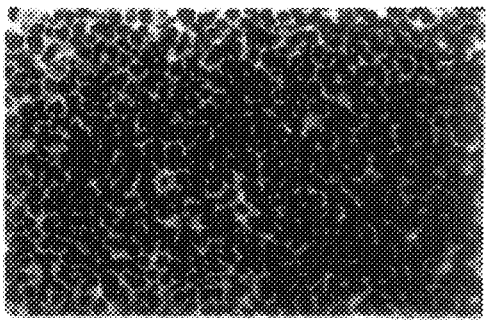
FIG. 8A2
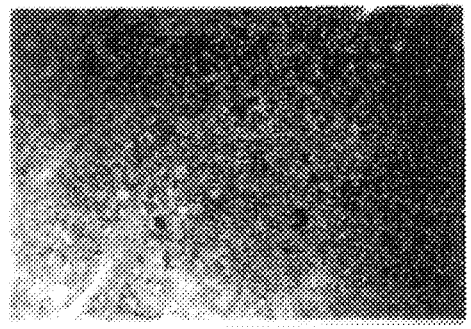
FIG. 8B1
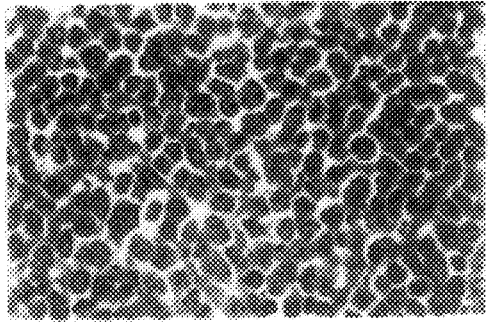
FIG. 8B2
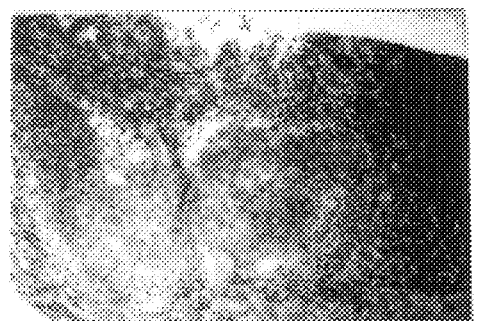
FIG. 8C1
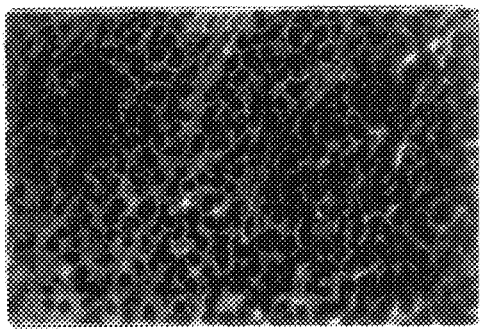
FIG. 8C2
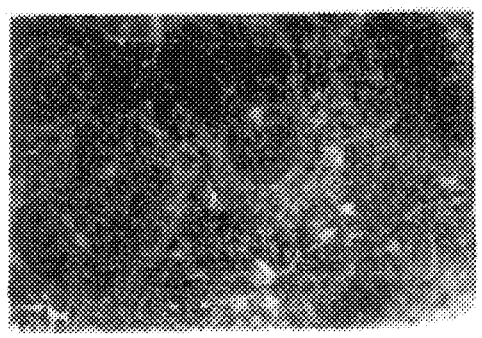
FIG. 8D1
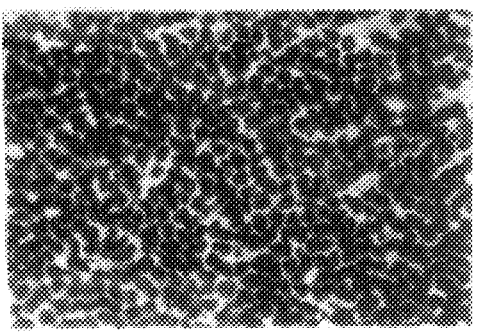
FIG. 8D2

(Day 20)

(Day 30)

(Day 38)

(Day 50)

5,858,988

POLY-SUBSTITUTED-PHENYL-OLIGORIBO NUCLEOTIDES HAVING ENHANCED STABILITY AND MEMBRANE PERMEABILITY AND METHODS OF USE

CROSS-REFERENCE TO RELATED APPLICATIONS

The present application is a continuation-in-part of U.S. application Ser. No. 08/200,650 filed Feb. 23, 1994, now U.S. Pat. No. 5,496,546, which is a continuation-in-part of U.S. application Ser. No. 08/022,055, filed Feb. 24, 1993, now abandoned.

BACKGROUND OF THE INVENTION

1. Field of the Invention

The present invention relates to the field of the delivery of antisense oligonucleotides. In particular, the present invention relates to antisense oligoribonucleotides conjugated to a carrier agent that enhances membrane permeability and stability of the antisense oligoribonucleotide constructs. Particularly preferred carrier agents include 2,4-dinitrophenyl- (DNP) and 3-fluoro-4,6-dinitrophenyl- (FDNP) groups coupled at the 2'-O position of the oligoribonucleotide.

2. Background of the Technology

Antisense oligonucleotides are nucleotide, or nucleotide analogues, whose sequence is complementary to a predetermined segment of RNA, either freshly transcribed RNA or messenger RNA (mRNA). Typically, sequences of the antisense oligonucleotides are chosen so as to be complementary to a critical sequence in a gene so that if the gene is hybridized to the complimentary antisense sequence, the gene cannot be expressed or is subjected to enzymatic degradation. See Stec et al. U.S. Pat. No. 5,151,510, the disclosure of which is hereby incorporated by reference in its entirety. A huge number of diseases conceivably can be mitigated, controlled, regulated, or prevented through the disabling of gene expression that antisense therapeutics allow. Thus, antisense oligonucleotides offer an incredible opportunity for the treatment of a large number of diseases.

For example, the use of antisense oligonucleotides has been proposed for the treatment of a broad range of viral infections. See Matsukura et al. PNAS 86:4244–4448 (1989), the disclosure of which is hereby incorporated by reference in its entirety.

Further, cancer is an area ripe with opportunities for antisense approaches. See WO 92/20348 the disclosure of which is hereby incorporated by reference in its entirety. Such application relates to antisense oligonucleotides to c-myb proto-oncogene in the treatment of colorectal cancer. See also Ensoli et al. WO 94/29,444 the disclosure of which is hereby incorporated by reference in its entirety. Such application relates to antisense oligonucleotides to basic fibroblast growth factor (bFGF) in the treatment of Kaposi's sarcoma. See further Bayever et al. *Antisense Res. and Dev.* 2:109–110 (1992) the disclosure of which is hereby incorporated by reference in its entirety. Such article discusses antisense oligoribodinucleotides to p53 for the treatment of acute myeloblastic leukemia (AML).

However, antisense oligonucleotides, while appearing to be exceptionally effective in certain tests, appear to suffer from several problems. It is postulated that the major limitations on antisense oligonucleotides for use in therapeutic applications is their apparent limited membrane permeability and high susceptibility to enzymatic degradation, both within and without cells. These two factors combine to limit both the concentration and the duration (half-life) of the oligonucleotides within cells. With such limited concentration and half-life of the oligonucleotides within the cells, it appears as though much of the therapeutic potential of the antisense oligonucleotides is lost.

Thus, researchers have expended considerable effort to overcome the problems of limited membrane permeability and high enzymatic degradation of antisense oligonucleotides. To this end, researchers have utilized a variety of techniques designed to increase membrane permeability and mitigate the enzymatic degradation of antisense oligonucleotides.

A detailed discussion of oligonucleotide design and synthesis is presented in Uhlmann et al. *Chenmcal Reviews* 90:543–584 (1990), the disclosure of which is hereby incorporated by reference in its entirety.

A preferred approach that has been used to enhance membrane permeability and stability of oligonucleotides is the use of alkyl-for-O substituted and S-for-O substituted nucleotide analogues. In connection with the alkyl substituted oligonucleotides, one of the phosphate oxygens that is not involved with the bridge between nucleotides is substituted with an alkyl group (particularly, methyl or ethyl). Similarly, in the S-substituted oligonucleotides (phosphorothioates), one of the phosphate oxygens that is not involved in the bridge is substituted with a sulfur. In the alkyl substituted oligonucleotides, a negatively charged oxygen is replaced with a neutral and sterically undemanding alkyl group (particularly methyl). With S-substituted oligonucleotides, the negative charge on the non-bridge oxygens is shared asymmetrically and located primarily on the sulfur. While, with each type of substituted oligonucleotide, membrane permeability and stability appear to be enhanced, two stereoisomers are prepared that require separation following synthesis or use of stereoselective synthetic methods. In S-substituted oligonucleotides, this problem can be minimized through the substitution of both of the non-bridge oxygens with sulfur (phosphorodithioates). Further, each type of these substituted oligonucleotides appear to suffer from a decreased hybridization potential with RNA in cells.

While inhibition of mRNA translation is possible utilizing either antisense oligoribonucleotides or oligodeoxyribonucleotides, free oligoribonucleotides are more susceptible to enzymatic attack by ribonucleases than oligodeoxyribonucleotides. Hence, oligodeoxyribonucleotides have generally been preferred because, upon hybridization with particular mRNA, the resulting DNA-RNA hybrid duplex is a substrate for RNase H, which specifically attacks the RNA portion of DNA-RNA hybrid at the free 2'-OH. Degradation of the mRNA strand of the duplex releases the antisense oligodeoxynucleotide strand for hybridization with additional messages from the gene.

With this problem in mind, a variety of other modified oligonucleotides have been synthesized to overcome this problem. See Uhlmann et al., supra. 2'-O-methyloligoribonucleotides have been synthesized and reportedly are completely resistant to RNA- and DNA-specific nucleases. See Sproat et al. Nucleic Acids Res. 17:3373 (1989), the disclosure of which is hereby incorporated by reference in its entirety. Less specific nucleases, however, cleave the 2'-O-methyloligoribonucelotides with varying efficiencies. Further, the same group reported the synthesis of other, larger, 2'-O-allyl-substituted oligoribonucleotides. See Iribarren et al. *Proc. Nat. Acad. Sci. U.S.A.*, 87:7747 (1990), the disclosure of which is hereby incorporated by reference in its entirety. The paper reports that 2'-O-(2-propylene)-oligoribonucleotides are more stable than 2'-O-methyloligoribonucleotides and show improved specific binding. A branched, five carbon allyl substituted oligoribonucleotide (2'-O-(3,3-dimethyl-2-butene)-oligoribonucleotide) also substantially improved the resistance of the oligonucleotide to nuclease digestion. However, such oligonucleotide showed a substantially reduced hybridization with complementary RNA sequences.

In addition, to the approaches described above for enhancing permeability and stability of oligonucleotides, a variety of groups have worked on incorporating oligonucleotides into specific carriers or binding oligonucleotides to specific or nonspecific delivery agents. For example, liposomal delivery of oligonucleotides appears to hold great promise. Limposomes are microscopic particles composed of mono- or multilamellar lipid bilayers which enter cells by phagocytosis or endocytosis. In addition to liposomes, pol-L-lysine has been used as a delivery agent to enhance interaction with cells. Other possible strategies are discussed by Uhlmann et al., supra. Nevertheless, there remains a need in the antisense oligonucleotide art for an effective approach to enhance the delivery of oligonucleotides. Further, there remains a need in the art for an effective approach to mitigate enzymatic degradation of oligonucleotides. Moreover, it would be advantageous if such benefits could be achieved without a substantial reduction in the hybridization potential of antisense oligonucleotides to cellular RNA.

SUMMARY OF THE INVENTION

In accordance with a first aspect of the present invention, there is provided an antisense oligoribonucleotide conjugated at the 2'-O position with a compound of the following general structure:

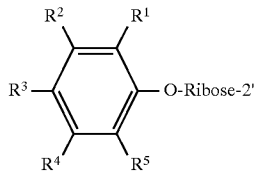

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$ as follows:

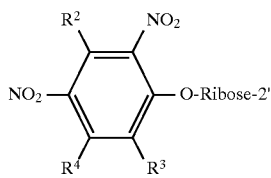

In another preferred embodiment, $R^2$, $R^4$, and $R^5$ are H. In a preferred embodiment, the oligoribonucleotide has a length of between 10 and 40 nucleotides. In another preferred embodiment, the oligoribonucleotide has a length of between 12 and 30 nucleotides. In another preferred embodiment, the oligoribonucleotide has a length of between 15 and 25 nucleotides.

In another preferred embodiment, at least one of the 5'-OH and 3'-OH ends of the oligoribonucleotide is conjugated with a compound of the following general structure:

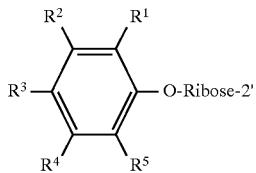

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$. In another preferred embodiment, $R^2$, $R^4$, and $R^5$ are H.

In accordance with a second aspect of the present invention, there is provided an antisense oligoribonucleotide derivatized at a plurality of 2'-O positions with a hydrophobic group selected from the group consisting of a 2,4-dinitrophenyl group and a 3-fluoro-4,6-dinitrophenyl group. In a preferred embodiment, the oligoribonucleotide has a length of between 10 and 40 nucleotides. In another preferred embodiment, the oligoribonucleotide has a length of between 12 and 30 nucleotides. In another preferred embodiment, the oligoribonucleotide has a length of between 15 and 25 nucleotides.

In accordance with a third aspect of the present invention, there is provided a method of enhancing membrane permeability and stability of an antisense oligoribonucleotide, comprising: providing an antisense oligoribonucleotide having a plurality of 2'-O positions, conjugating a compound of the following general structure to the 2'-O position of the oligoribonucleotide:

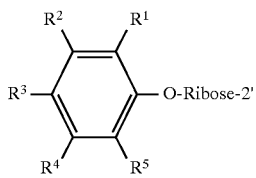

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$. In another preferred embodiment, $R^2$, $R^4$, and $R^5$ are H. In a preferred embodiment, the oligoribonucleotide has a length of between 10 and 40 nucleotides. In another preferred embodiment, the oligoribonucleotide has a length of between 12 and 30 nucleotides. In another preferred embodiment, the oligoribonucleotide has a length of between 15 and 25 nucleotides. In another preferred embodiment, at least one of the 5'-OH and 3'-OH ends of the oligoribonucleotide is conjugated with a compound of the following general structure:

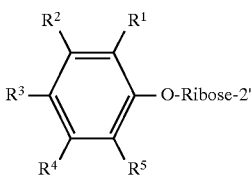

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate. In a preferred embodiment, $R^1$ and $R^3$ are $NO_2$. In another preferred embodiment, $R^2$, $R^4$, and $R^5$ are H.

In accordance with a fourth aspect of the present invention, there is provided an improved antisense therapeutic method, comprising administering an antisense oligonucleotide comprising a plurality of 2'-O positions in a manner designed inhibit gene expression, the improvement comprising: derivatizing the antisense oligonucleotide at a plurality of the 2'-O positions with a compound of the following structure:

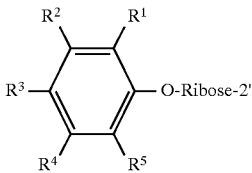

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate.

In a preferred embodiment, $R^1$ and $R^3$ are $NO_2$. In another preferred embodiment, $R^2$, $R^4$, and $R^5$ are H. In another preferred embodiment, the oligoribonucleotide has a length of between 10 and 40 nucleotides. In another preferred embodiment, the oligoribonucleotide has a length of between 12 and 30 nucleotides. In another preferred embodiment, the oligoribonucleotide has a length of between 15 and 25 nucleotides. In another preferred embodiment, at least one of the 5'-OH and 3'-OH ends of the oligoribonucleotide is conjugated with a compound of the following general structure:

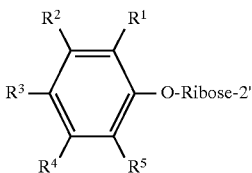

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate. In another preferred embodiment, $R^1$ and $R^3$ are $NO_2$. In another preferred embodiment, $R^2$, $R^4$, and $R^5$ are H.

In accordance with a fifth aspect of the present invention, there is provided an improved antisense therapeutic method, comprising administering an antisense oligonucleotide comprising a plurality of 2'-O positions in a manner designed inhibit gene expression, the improvement comprising: derivatizing the antisense oligonucleotide at a plurality of the 2'-O positions with a group selected from the group consisting of a 2,4-dinitrophenyl group and a 3-fluoro-4,6-dinitrophenyl group. In a preferred embodiment, the oligoribonucleotide has a length of between 10 and 40 nucleotides. In another preferred embodiment, the oligoribonucleotide has a length of between 12 and 30 nucleotides. In another preferred embodiment, the oligoribonucleotide has a length of between 15 and 25 nucleotides. In another preferred embodiment, at least one of the 5'-OH and 3'-OH ends of the oligoribonucleotide is conjugated with a compound of the following general structure:

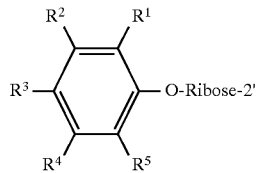

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphothioate. In another preferred embodiment, $R^1$ and $R^3$ are $NO_2$. In another preferred embodiment, $R^2$, $R^4$, and $R^5$ are H.

BRIEF DESCRIPTION OF THE DRAWING FIGURES

■ [$^{14}$C] DNP-poly [A] into lymphocytes;
△ [$^{14}$C] DNP-poly [A] into leukocytes;
○ [$^{14}$C] poly [A] into lymphocytes; and
● [$^{14}$C] poly [A] into leukocytes.

Figure 3:
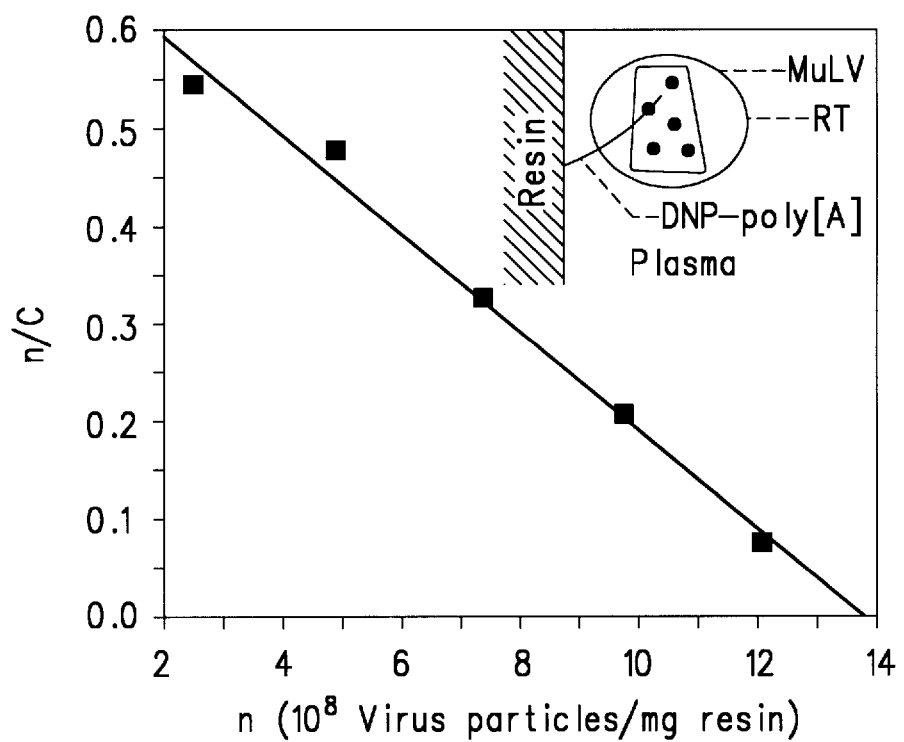

FIG. 3 is a graph showing the observed binding equilibrium of MuLV in human plasma to acrylamide beads covalently attached to DNP-poly [A]. The inset shows the assumed mode of binding.

Figure 4:
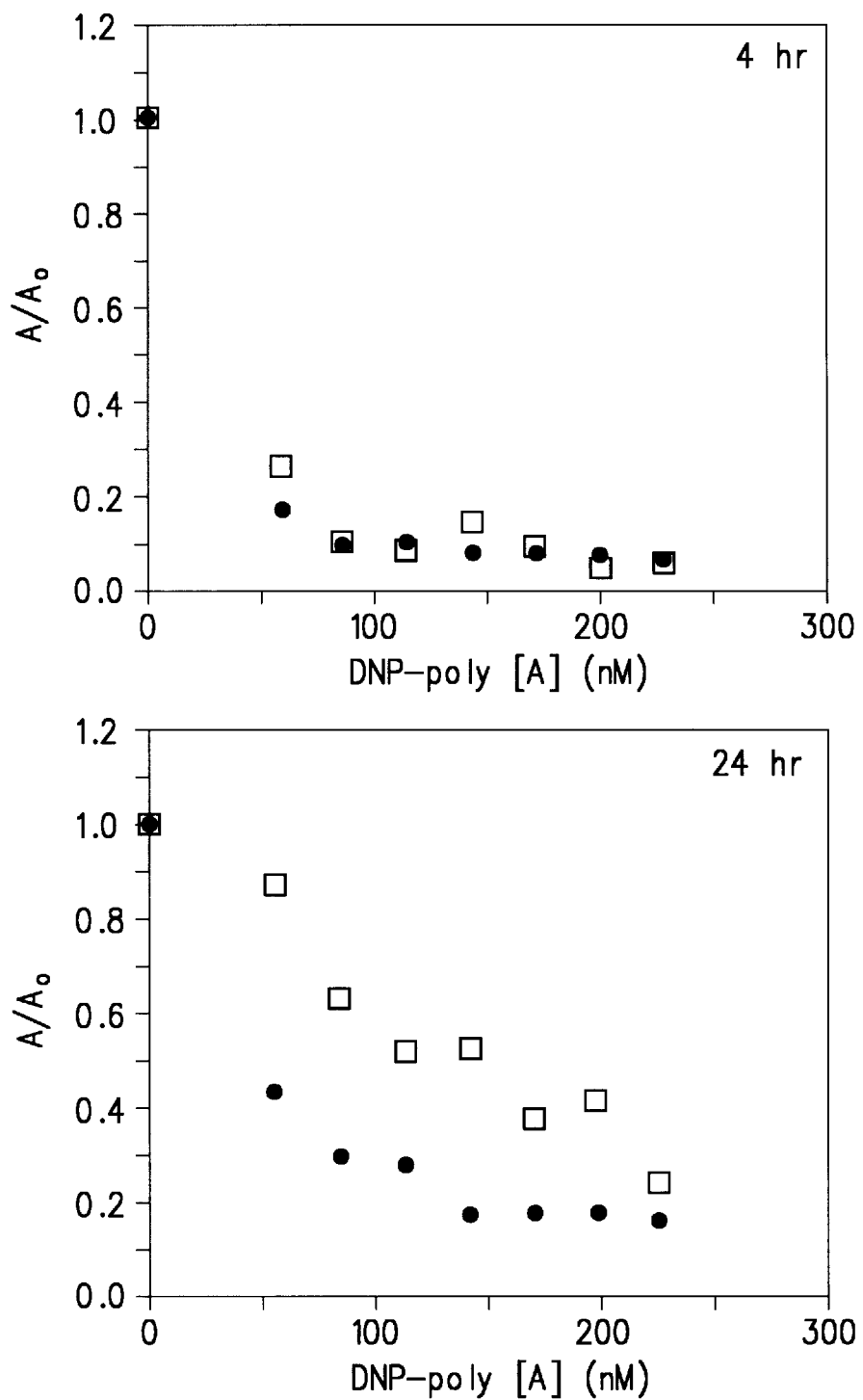

FIG. 4 is two graphs showing the effects of 4 hour and 24 hour preincubation at 37° C. on the inhibition potency of DNP-poly [A] on 25 nM concentration of HIV RT, as follows:

□ preincubation in 0.01M HCl; and
● preincubation in DEPC-treated water.

Figure 5:
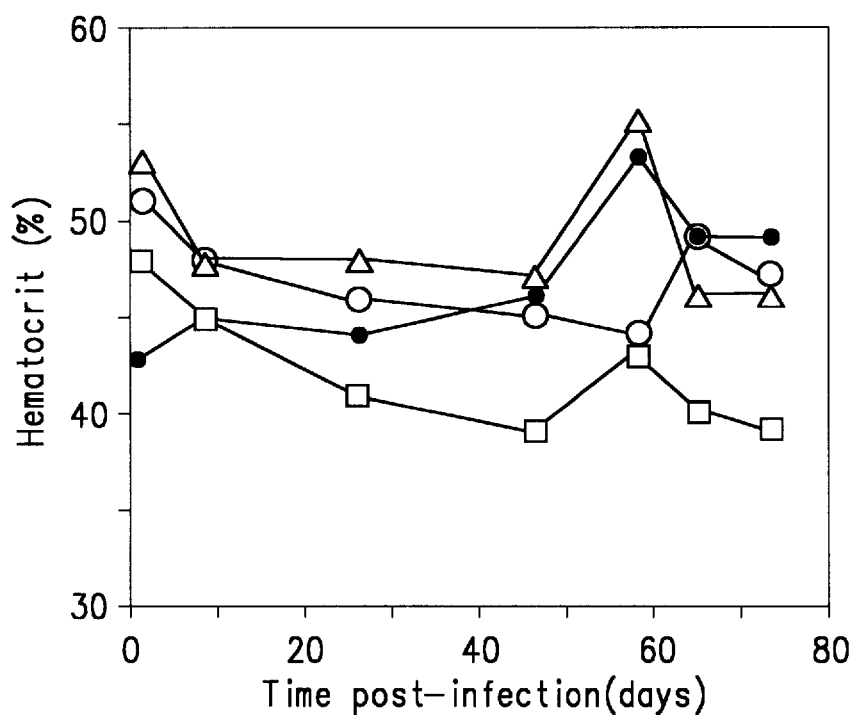
Figure 6A:
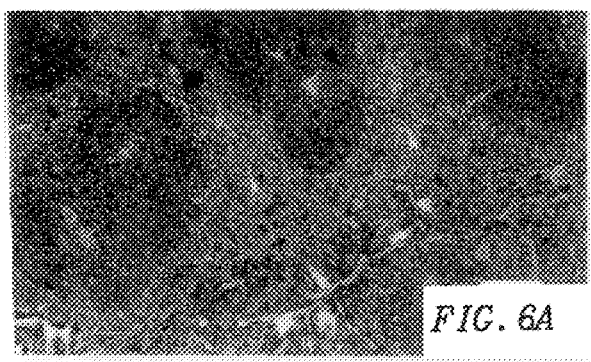
Figure 6B:
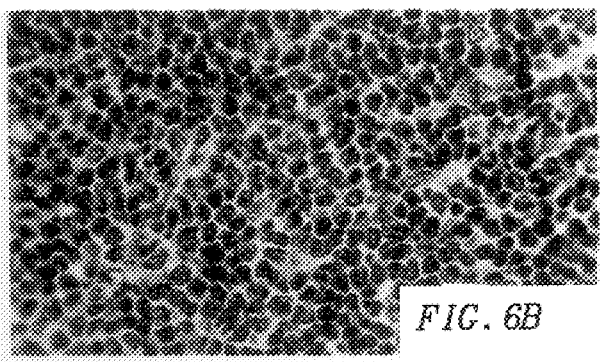
Figure 6C:
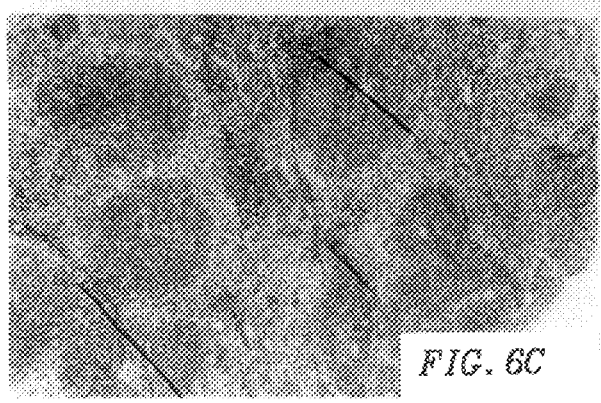
Figure 6D:
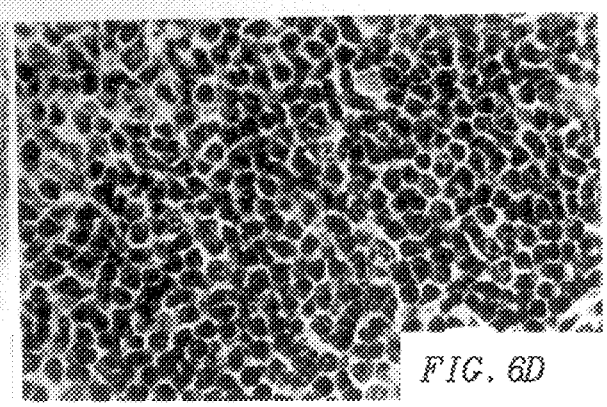
Figure 7A:
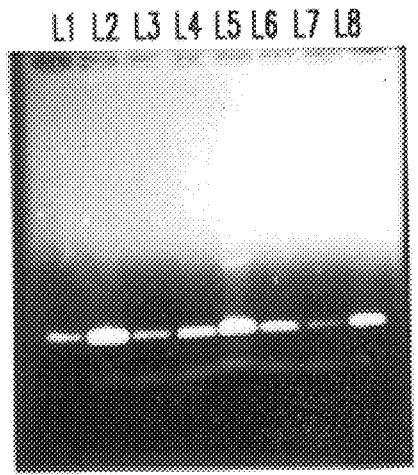
Figure 7B:
Figure 7C:
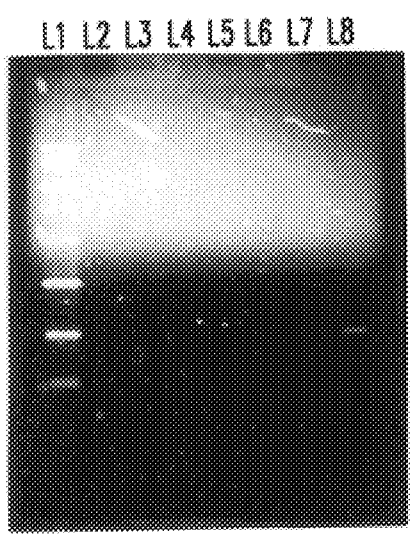
Figure 7D:
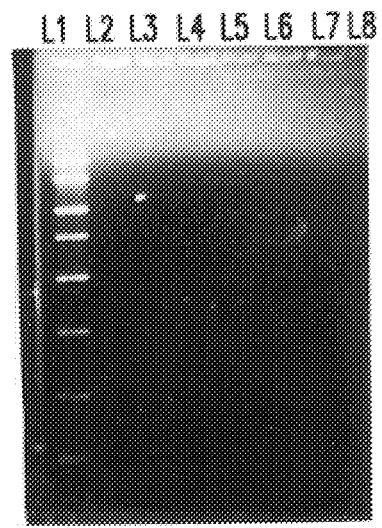
Figure 9A:
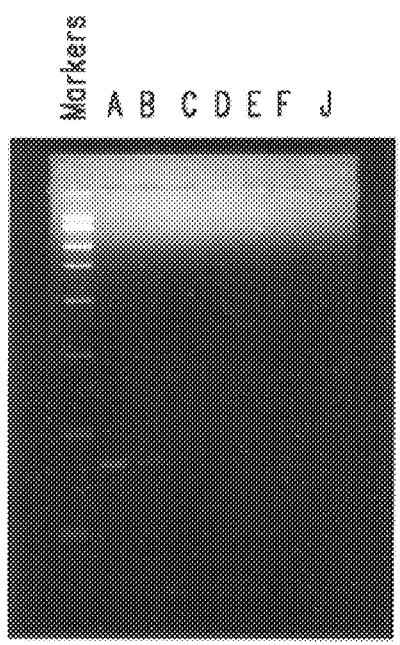
Figure 9B:
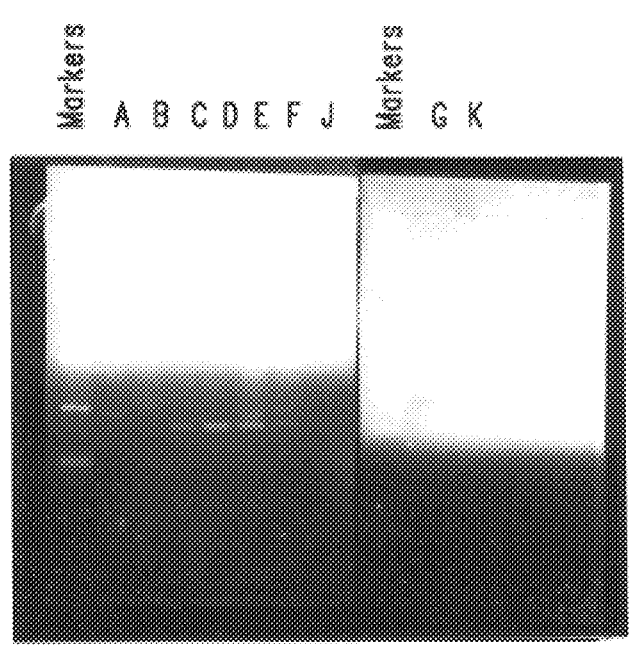
Figure 9C:
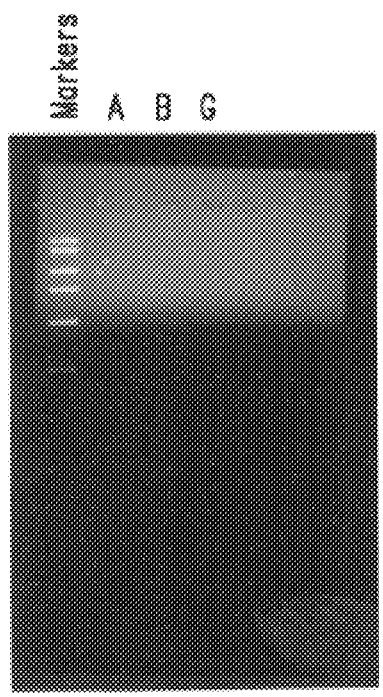
Figure 9D:
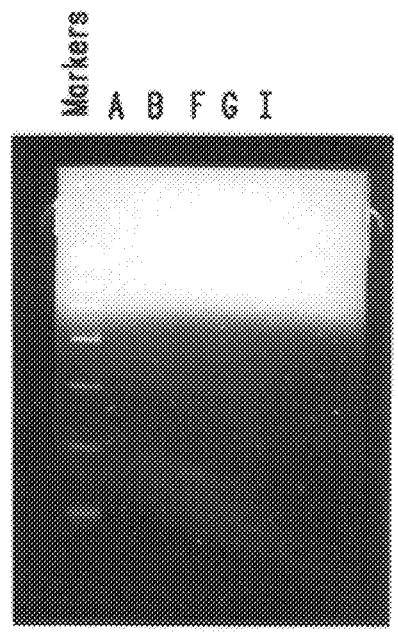

FIG. 5 is a graph showing hematocrit readings for mice infected with $10^4$–$10^5$ virus particles i.p. at 1–73 days after injection, as follows:

□ viremia;
● normal;
○ drug (1–10 mg DNP-poly [A]/kg in one dose); and
△ viremia+drug (1–10 mg DNP-poly [A]/kg in one dose).

FIG. 6 is a series of photomicrographs showing sections of spleens from mice that were treated with 10 mg of DNP-poly [A], 3 times over 1 week, immediately after virus injection, as follows:

(A) infected and treated (160×);

(B) infected and treated (1600×);

(C) unifected but treated (160×); and (D) uninfected but treated (1600×).

The mice were sacrificed at approximately 3 months after virus infection. The spleens were preserved in formalin and subsequently stained with hematoxylin and eosin (H & E).

FIG. 7 is a series of photographs of electrophoresis gels showing the effect on mice that were infected with $10^8$ virus particles of MuLV when treated with 100 mg DNP-poly [A]/kg body weight. The mice were infected for up to four months and then treated with DNP-poly [A] by i.p. injection, as follows:

(A) shows the results prior to treatment (Lanes 1–8 correspond to mouse numbers 1–8);

(B) shows the results after 1 week of treatment (Lanes 1–8 correspond to mouse numbers 1–8);

(C) shows the results two weeks after treatment (Lane 1=PCR Ladder; Lane 2=normal mouse; Lane 3=mouse 1; Lanes 4–7 correspond to mouse numbers 3–6; and Lane 8=mouse 8).

(D) shows the results three weeks after treatment (Lane 1=PCR Ladder; Lane 2=mouse 1; Lanes 3–6 correspond to mouse numbers 3–6; Lane 7=mouse 8; and Lane 8=normal mouse).

FIG. 8 is a series of photomicrographs showing immunohistochemistry of spleens of mice used in the experiments related to DNP-poly [A], as follows: (A) normal mouse spleen at (1) 160× and (2) 1600×;

(B) infected ($10^9$ virus particles) and untreated spleen at (1) 160× and (2) 1600×;

(C) infected with $10^9$ virus particles for four months and treated 3× per week with 100 mg DNP-poly [A]/kg at (1) 160× and (2) 1600×; and (D) uninfected but treated 3× per week with 100 mg DNP-poly [A]/kg at (1) 160× and (2) 1600×.

FIG. 9 is a series of photographs of electrophoresis gels showing the results of RT-PCR assays on mice infected with MuLV and demonstrating the abolition of the virus in mice treated with a DNP-derivatized antisense oligoribonucleotide to the MuLV envelope protein.

DETAILED DESCRIPTION OF THE INVENTION

In accordance with the present invention, it has been unexpectedly discovered that through the simple derivatization of antisense oligonucleotides at the 2'-O position with a hydrophobic carrier agent, suitably, 2,4-dinitrophenyl groups or 3-fluoro-4,6-dinitrophenyl groups, the resulting derivatized antisense oligonucleotides are rendered substantially more membrane permeable and are extremely resistant to enzymatic degradation. In accordance with the invention, it is therefore possible to use "natural" oligonucleotides (i.e., those oligonucleotides formed from naturally occurring nucleotides). Beneficially, the use of natural antisense oligonucleotides improves hybridization of the antisense sequence with the sense RNA strand. This fact improves the therapeutic potential of any given antisense approach.

Oligonucleotides derivatized in accordance with the invention withstand extreme conditions in which their underivatized brethren would completely fail. Further, oligonucleotides derivatized in accordance with the invention are exceptionally bioavailable and appear to pass through cell membranes in tissue culture as well as in vivo in mammals. In contrast, underivatized oligonucleotides are substantially less bioavailable. Ultimately, oligonucleotides derivatized in accordance with invention appear to be substantially nontoxic to cells and well tolerated in mammals.

As mentioned above, while natural oligonucleotides are preferably used in accordance with the invention, it is expected that virtually any oligonucleotide or oligonucleotide analogue containing a 2'-OH can be derivatized and used with similar benefits of enhanced membrane permeability and stability as natural oligonucleotides. Further, while it is not believed to be necessary, the derivatized oligonucleotides of the invention can be delivered using conventional delivery vehicles and agents that have been used in the art to enhance delivery of oligonucleotides, such as liposomes, cationic lipids, and the like.

In general, appropriate hydrophobic carrier agents in accordance with the invention have the following general structure:

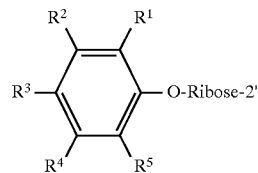

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched O-acyl, linear or branched 0-alkylene, linear or branched amido, linear or branched S-alkyl, linear or branched S-acyl, linear or branched S-alkylene, mono or disubstituted amine, linear or branched amido, linear or branched thioamido, phosphothionate, or phosphothioate. Preferably, no one of $R^1$, $R^2$, $R^3$, $R^4$, and $R^5$ exceeds 9 atoms excluding protons.

In a preferred embodiment, $R^1$ and $R^3$ are $NO_2$ and $R^2$, $R^4$, and $R^5$ are as above, as follows:

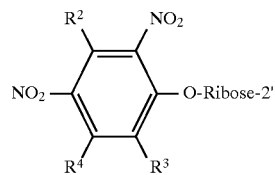

It will be appreciated that when $R^2$, $R^4$, and $R^5$ are H, the compound is DNP.

In another preferred embodiment, the $R^1$ and $R^3$ are $NO_2$, $R^2$ and $R^5$ are as described above, and $R^4$ is a halide (fluorine), as follows:

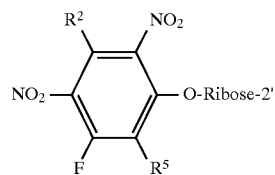

It will be appreciated that when $R^2$ and $R^5$ are H, the compound is FDNP.

In a preferred embodiment, the hydrophobic carrier agents of the present invention as described above are conjugated to oligonucleotides for the purpose of stabilizing and enhancing delivery of antisense oligonucleotides.

As used herein, the term "oligonucleotide" includes not only oligomers and polymers of the common biologically significant nucleotides, i.e., the nucleotides adenine ("A"), guanine ("G"), cytosine ("C"), thymine ("T") and uracil ("U"), but also include oligomers and polymers hybridizable to an RNA transcript of the particular gene of interest which may contain other nucleotides. Likewise, the term "oligonucleotides" may include oligomers and polymers wherein one or more purine or pyrimidine moieties, sugar moieties or internucleotide linkages is chemically modified. The term "oligonucleotide" is thus understood to also include oligomers which may not properly be designated as "oligonucleotides" because of modification of the internucleotide phosphodiester bond. Such modified oligonucleotides include, for example, the alkylphosphonate oligonucleotides, discussed below.

The term "phosphorothioate oligonucleotides" is defined as an oligonucleotide wherein one more of the internucleotide linkages is a phosphorothioate group,

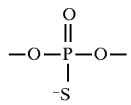

as opposed to the common phosphodiester group

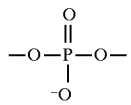

which is characteristic of unmodified oligonucleotides.

An "alkylphosphonate oligonucleotide" is defined as an oligonucleotide wherein one or more of the internucleotide linkages is an alkylphosphonate group,

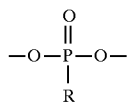

where R is an alkyl group preferably methyl or ethyl.

The term "gene RNA transcript" is defined herein as the RNA transcript encoding the protein of interest. It will be understood that a variety of methods for determining the level of a gene's expression are well-known to those skilled in the art. Such methods include, for example, reverse transcriptase polymerase chain reaction (RT-PCR) analysis.

The antisense oligonucleotides of the present invention may be synthesized by any of the known chemical oligonucleotide synthesis methods. Such methods are generally described, for example, in Winnacker *From Genes to Clones: Introduction to Gene Technology*, VCH Verlagsgesellschaft mhH (H. Ibelgaufts trans. 1987), the disclosure of which is hereby incorporated by reference in its entirety. Any of the known methods of oligonucleotide synthesis may be utilized in preparing the instant antisense oligonucleotides.

The antisense oligonucleotides are most advantageously prepared by utilizing any of the commercially available, automated nucleic acid synthesizers. One such device, the Applied Biosystems 380B DNA Synthesizer, utilizes β-cyanoethyl phosphoramidite chemistry. Further, many antisense oligonucleotides are commercially available. For example, Oligo Therapeutics, Inc. has a broad line of commercially available oligonucleotides and, further, provides contract manufacturing services for the preparation of oligonucleotides.

Since the complete nucleotide sequence of DNA complementary to many gene RNA transcripts are known, antisense oligonucleotides hybridizable with any portion of the particular gene transcript may be prepared by oligonucleotide synthesis methods known to those skilled in the art.

Prior work indicates that while any length oligonucleotide may be utilized in the practice of antisense therapeutics, sequences shorter than 10 to 12 bases may be less specific in hybridizing to the target gene RNA. Further, such sequences may be more easily destroyed by enzymatic digestion within and without cells. In addition, such sequences may be destabilized by enzymatic digestion. Hence, oligonucleotides having 10 to 12 or more nucleotides are preferred.

Prior work has also shown that long sequences, particularly sequences longer than about 40 nucleotides, may be somewhat less effective in inhibiting gene translation because of decreased uptake by the target cell. It is believed that the present invention is less susceptible to this problem owing to the coupling of the antisense oligonucleotide with the carrier groups. Nevertheless, oligomers of 10–40 nucleotide residues are preferred, more preferably 12–30 nucleotide residues, most preferably 15–25 nucleotide residues. Thus, sequences of 15–25 nucleotide residues are most particularly preferred. In connection with the present invention, membrane permeability and stability to enzymatic degradation of derivatized oligonucleotides is essentially not a problem. Therefore, the choice of the length of any particular nucleotide sequence will revolve around the ability of the oligonucleotide to form a stable hybrid with the particular RNA transcript and the stability of the duplex hybrid to enzymatic degradation.

Oligonucleotides complementary to and hybridizable with any portion of the particular gene transcript can, in principle, be effective for inhibiting translation of the transcript, and capable of inducing the effects herein described. It appears that translation is often most effectively inhibited by blocking the RNA at a site at or near the initiation codon. Thus, oligonucleotides complementary to the 5'-terminal region of the gene RNA transcript are often used. It is believed that secondary or tertiary structure which might interfere with hybridization is minimal in this region. Moreover, it has been suggested that sequences that are too distant in the 3'-direction from the initiation site may be less effective in hybridizing the RNA transcripts because of a "read-through" phenomenon whereby the ribosome is postulated to unravel the antisense/sense duplex to permit translation of the message. See, e.g., Shakin, *J. Biochemistry* 261:16018 (1986). Similarly, antisense oligonucleotides can additionally be directed to a site at or near a splice donor-acceptor sites. For example, in the case of basic fibroblast growth factor (bFGF), which contains two splice donor-acceptor sites, oligonucleotides can be directed to the splice donor-acceptor site 1 (codon 60) or splice donor-acceptor site 2 (codon 94–95). See Ensoli et al. WO 94/29,444.

Ensoli et al. point out that in respect of bFGF, it is preferable to utilize antisense oligomers that are complementary to one of the two splice donor-acceptor sites of the bFGF transcript, and, particularly the region including the first splice donor-acceptor site. In the case of other genes, it will be appreciated that useful antisense oligomers are not limited to that complementary to the sequences found in the translated portion of the RNA transcript, but also includes oligomers complementary to nucleotide sequences including the initiation codon, or contained in, or extending into, the 5'-and 3'-untranslated regions.

The S1 nuclease assay procedure of *Molecular Cloning, 2nd edition* (Sambrook et al., Eds. 1989), pages 7.66–7.70 (incorporated herein by reference) can be utilized to map the location of cap sites using RNA isolated from cell lines expressing the gene. The location of the longest clearly visible band can be located as indicative of the putative principle cap site. S1 protection assays may also be used to reveal faint bands in addition to the main band corresponding to the cap site. These other bands may represent rare or unstable transcripts of the gene. Multiple sites of transcription initiation are not uncommon in genes which lack a perfect TATAA box. The nucleotide sequence of the RNA transcript 5'-terminus beginning with the cap nucleotide may be readily established, and antisense oligonucleotides complementary and hybridizable thereto may be prepared.

The oligonucleotide employed may represent an unmodified oligonucleotide or an oligonucleotide analog. Thus, oligonucleotides hybridizable to the particular gene RNA transcript finding utility according to the present invention include not only oligomers of the biologically significant native nucleotides but also oligonucleotide species which have been modified for improved stability and/or lipid solubility. For example, it is known that enhanced lipid solubility and/or resistance to nuclease digestion results by substituting an alkyl or alkoxy group for a phosphate oxygen in the internucleotide phosphodiester linkage to form an alkylphosphonate oligonucleotide or alkylphosphotriester oligonucleotide. However, such alkyl substituted oligonucleotides suffer from the problem that, owing to steric and electrochemical interactions, may not hybridize as well as natural oligonucleotides. The phosphorothioates are also stable to nuclease cleavage and soluble in lipid. They may be synthesized by known automatic synthesis methods. Phosphorothioates, however, have been identified as possessing similar potential hybridization problems as the alkyl substituted oligonucleotides. Non-ionic oligonucleotides such as alkyl substituted and phosphorothioates, are characterized by increased resistance to nuclease hydrolysis and/or increased cellular uptake, while retaining the ability to form reasonably stable complexes with complementary nucleic acid sequences. The alkylphosphonates in particular, are stable to nuclease cleavage and soluble in lipid. The preparation of alkylphosphonate oligonucleotides is disclosed in U.S. Pat. No. 4,469,863. The methylphosphonates, in particular, are preferred. Methylphosphonate oligomers can be prepared by a variety of methods, both in solution and on insoluble polymer supports (Agrawal et al. *Nucl. Acids Res.* 6:3009–3024 (1979)).

The most efficient procedure currently known for preparation of methylphosphonate oligonucleotides involves use of 5'-O-dimethoxytrityldeoxynucleotide-3'-O-diisopropylmethylphosphoramidite intermediates, which are similar to the methoxy or β-cyanoethyl phosphoramidite reagents used to prepare oligodeoxyribonucleotides. The methylphosphonate oligomers can be prepared on controlled pore glass polymer supports using an automated DNA synthesizer (Sarin et al. *Proc. Natl. Acad. Sci. USA* 85:7448–7451 (1988)).

Resistance to nuclease digestion may also be achieved by modifying the internucleotide linkage at both the 5' and 3' termini with phosphoroamidites according to the procedure of Dagle et al. *Nucl. Acids Res.* 18:4751–4757 (1990). Suitable nucleotide analogues for preparation of the antisense oligonucleotides described herein include but are not limited to the ethyl or methyl phosphonate analogues disclosed in U.S. Pat. No. 4,469,863.

Phosphorothioate oligonucleotides contain a sulfur-for-oxygen substitution in the internucleotide phosphodiester bond. Phosphorothioate oligonucleotides combine the properties of reasonably effective hybridization for duplex formation with substantial nuclease resistance, while retaining the water solubility of a charged phosphate analogue. The charge is believed to confer the property of cellular uptake via a receptor (Loke et al. *Proc. Natl. Acad. Sci. USA* 86:3474–3478 (1989)).

Phosphorothioate modified oligodeoxynucleotide are described by LaPlanche et al. *Nucleic Acids Research* 14:9081 (1986) and by Stec et al. *J. Am. Chem. Soc.* 106:6077 (1984). The general synthetic method for phosphorothioate oligonucleotides was modified by Stein et al. *Nucl. Acids Res.* 16:3209–3221 (1988), so that these compounds may readily be synthesized on an automatic synthesizer using the phosphoramidite approach. Also, additional modifications have been added by Zon et al. Zon et al. *Anti-Cancer Drug Design* 6:539–568 (1991); Zon et al. *Oligonucleotides and Analogues: A Practical Approach*, F. Eckstein, Ed. (Oxford University Press, Oxford, England), pp. 87–108 (1991)). See also Stec et al. U.S. Pat. No. 5,151,510.

Furthermore, recent advances in the production of oligoribonucleotide analogues mean that other agents may also be used for the purposes described here, e.g., 2'-O-methylribonucleotides (Inove et al. *Nucleic Acids Res.* 15:6131 (1987)) and chimeric oligonucleotides that are composite RNA-DNA analogues (Inove et al. *FEBS Lett.* 215:327 (1987)).

In general, the antisense oligonucleotides of the present invention will comprise a sequence which is completely complementary to the target portion of the message from the gene. Absolute complementarity is not however required, particularly in larger oligomers. Thus, reference herein to a "nucleotide sequence complementary to at least a portion of the RNA transcript" of a particular gene does not necessarily mean a sequence having 100% complementarity with the transcript. In general, any oligonucleotides having sufficient complementarity to form a stable duplex with RNA of the gene is suitable.

Stable duplex formation depends upon the sequence and length of the hybridizing oligonucleotide and the degree of complementarity with the target region of the message from the gene. Generally, the larger the hybridizing oligomer, the more mismatches that can be tolerated. One skilled in the art can readily determine the degree of mismatching that can be tolerated between any given antisense oligomer and the target message from the gene sequence, based upon the melting point, and therefore the stability, of the resulting duplex. Melting points of duplexes of given base pair composition can be readily determined from standard texts, such as *Molecular Cloning: A Laboratory Manual* (2nd edition, 1989), J. Sambrook et al, Eds., the disclosure of which is hereby incorporated by reference in its entirety.

While oligonucleotides capable of stable hybridization with any region of the message for a particular gene are within the scope of the present invention, oligonucleotides complementary to a region including the initiation codon or a splice donor-acceptor site are believed particularly effective.

Earlier work performed and overseen by the inventor related to FDNP-and DNP-poly[A] oligonucleotides for use in the treatment of viral infections, and, particularly the treatment of HIV. See U.S. patent application, Ser. No. 08/200,650, filed on Feb. 23, 1994, which is a continuation-in-part of U.S. patent application, Ser. No. 08/022,055, filed on Feb. 24, 1993, the disclosures of which are hereby incorporated by reference in their entirety. That work originated based on the long-standing practice of labelling nucleophilic groups of proteins with Sanger's reagent 1-fluoro-2,4-dinitrobenzene. Thus, poly[A] was reacted with electrophilic 3-fluoro-4,6-dinitrophenyl (FDNP) or 1-fluoro-2,4-dinitrobenzene (FDNB) to derivative poly[A] at its 2'-OH positions through ether linkages. See Chuan and Wang, *J. Biol. Chem.* 263:13003 (1981), the disclosure of which is incorporated herein by reference in its entirety. These electrophilic groups serve to react with and to bind to nucleophilic groups in the active site cleft of reverse transcriptase, thus blocking its action. The structure of the resulting polymer derivative, designated as FDNP-poly[A], is represented by a structure shown below with general formula: $M_n(FDNP)_m X_i[A]$.

where: $[A]_n$=polyadenylic acid (5') with n adenylic acid residues,

FDNP=3-fluoro-4,6-dinitrophenyl groups, attached covalently to m of the n 2'-OH groups of $[A]_n$ via ether linkage, X=an acyl group, i=0 or 1, M=a cation selected to provide a desired degree of solubility for the composition, and has one of the generic structures:

Indeed, while the action of DNP-poly[A] is not irreversible it was found that with 1 DNP-group per 1.5 adenine residues, the latter is about twelve times as effective (i.e., is equally effective at one-twelfth the dosage) as is FDNP-poly[A]. The polymer derivative, designated as DNP-poly[A], is represented by a structure shown below with general formula: $M_n(DNP)_m X_i[A]_n$ where: $[A]_n$=polyadenylic acid (5') with n adenylic acid residues, DNP=2,4-dinitrophenyl groups, attached covalently to m of the n 2'-OH groups of $[A]_n$ via ether linkage, X=an acyl group, i=0 or 1, M=a cation selected to provide a desired degree of solubility for the composition, and has one of the generic structures:

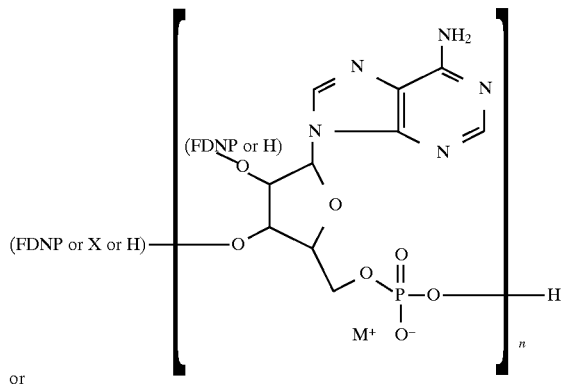

or

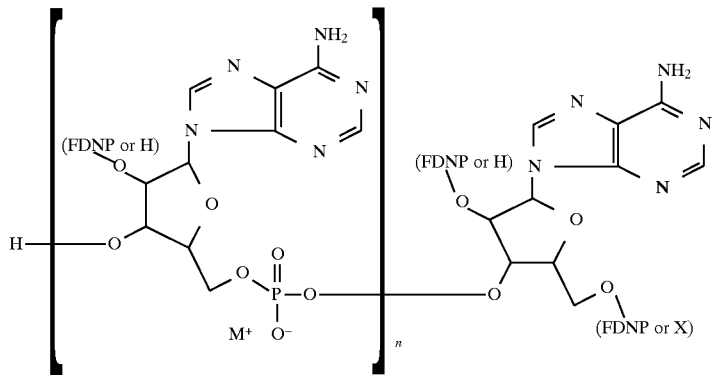

It was further discovered that DNP-poly[A] is also effective in inactivating reverse transcriptases and ribonucleases.

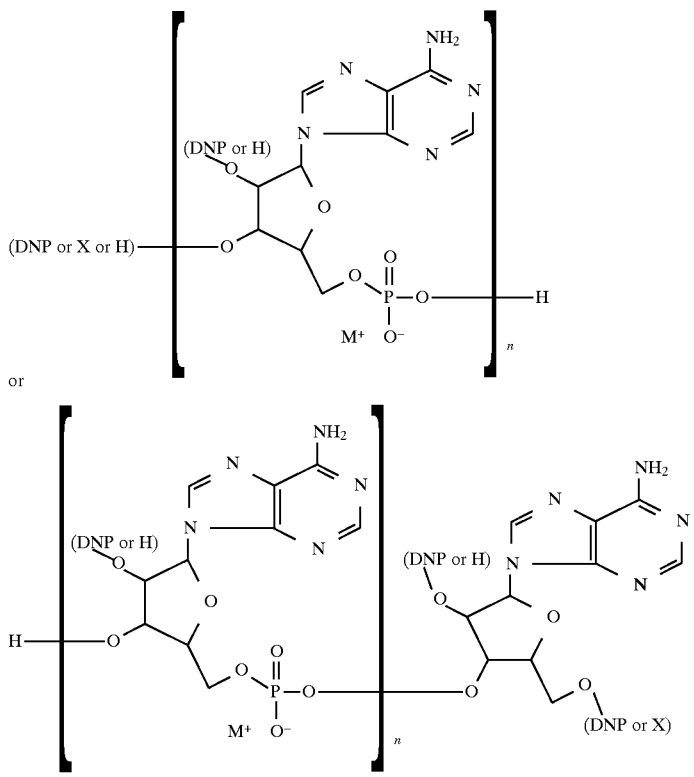

In both cases, n is sufficiently large so that the Y-poly[A] (where Y=DNP, FDNP or where some Y are DNP and others are PDNP) substantially completely fills the active site cleft of the RNA-virus RT to effectively inactivate the reverse transcriptase and/or can effectively inactivate ribonuclease. Generally it is preferred that n be relatively large, suitably 20 or greater and preferably 25 or greater. Actual experiments are set forth below for a relatively higher molecular weight Y-poly[A](h-$M_r$), n≈270, m≈69, $M_r$≈1.1×10$^5$ (where $M_r$ represents molecular weight) and for a relatively lower molecular weight Y-poly[A](1-$M_r$), n≈28, m≈9, $M_r$≈1.2×10$^4$.

FDNP groups are generally attachable to the poly[A] to provide a ratio of FDNP group to [A] of no more than about 1:4. DNP groups are attachable to the poly[A] to provide a considerably higher ratio of about 1:1.5. Mixed FDNP/DNP poly[A] polymers can also be formed. Generally, 1,3-difluoro-2,4-dinitrobenzene (DFDB) will first be reacted with the poly[A] to provide a ratio of FDNP to [A] of from about 1:4 to about 1:10. Then, the product will be reacted with 1-fluoro-2,4-dinitrobenzene (FDNB) so that the resulting composition will have an overall ratio of FDNP plus DNP groups to [A] which is as high as can be attained, generally of greater than 1:4, preferably greater than 1:2. Similar ratios of the hydrophobic carrier agent to nucleotide sequence are contemplated in accordance with the invention.

The cation, M, can be any cation which will provide a sufficient concentration of the composition to accomplish a desired purpose. While the potassium salt is preferred, ammonium, rubidium, cesium, among other salts can be utilized in its place.

Since the Y-poly[A] polymers were designed to inactivate all reverse transcriptases, they can be utilized for the treatment of virtually any diseases caused by RNA-viruses, e.g., adult T-cell leukemia/lymphoma, hepatitis A, C, D and E, influenza, parainfluenza, infant bronchiolitis and pneumonia, common cold, measles, mumps, etc. Thus, diseases caused by, by way of non-limiting example, the RNA-viruses HTLV (adult T-cell leukemiallymphoma virus), HAV (Hepatitis A virus), HAC (Hepatitis C virus), HDV (Hepatitis D virus), HAC (Hepatitis E virus), HEV (influenza virus), parainfluenza virus, RSV (respiratory syncytial virus), common cold causing coronavirus and rhinovirus, measles virus and mumps virus can be controlled by use of the Y-poly [A] compounds.

It has unexpectedly been discovered in accordance with the present invention that highly variable sequences of polynucleotides can be derivatized in a similar manner to poly [A]. Moreover, when derivatized with a hydrophobic carrier agent in accordance with the present invention, such as DNP or FDNP, such oligonucleotides are readily and stably available to cells. This discovery provides another route to the treatment of diseases such as the foregoing, and many others, through enhanced delivery of highly stable oligonucleotides for antisense applications, among others. Thus, in accordance with the present invention, another approach to RNA-virus mediated or caused diseases is provided and such diseases can be controlled by use of derivatized polynucleotides in accordance with the invention.

As will be appreciated, in the antisense oligonucleotides of the present invention, possess a structure similar to those illustrated above for poly [A], with the exception that, instead of strictly adenine groups, the compounds possess the sequences of the individual nucleotides. It will also be appreciated that antisense oligonucleotides derivatized in accordance with the invention possess both the enhanced membrane permeability and resistance to enzymatic degradation that is observed with derivatized poly [A]. In addition, however, the presence of the antisense sequence enables highly specific action of the compositions of the invention on particular genes. That is to say that while derivatized poly [A] appears to possess a general action on reverse transcriptases, derivatized antisense oligonucleotides in accordance with the present invention have very specific action on whatever gene they are designed to hybridize.

In the disclosure that follows, several experiments are described that have been conducted relating to the Moloney murine leukemia virus (MuLV). First, work performed by and under the direction of the inventor has demonstrated that DNP-poly [A] is effective in the treatment of MuLV in mammals. Such work provides a back drop for recent work related to the preparation and effectiveness of antisense oligonucleotides, where it has been demonstrated that a DNP derivatized antisense oligonucleotide to block the synthesis of the MuLV envelope protein results in abrogation of MuLV infection in mammals.

The MuLV virus is originated from Sarcoma 37. It is a transplantable connective tissue neoplasm of mice. Moloney, J. B "Biological studies on a lymphoid leukemia virus extracted from sarcoma 37.1. Origin and introductory investigations" *J. Natl. Cancer Inst.* 24:933–951 (1960), the disclosure of which is hereby incorporated by reference. It has been reported to produce a generalized lymphocytic neoplasm in mice within a short period (Dunn et al. "Pathogenesis of virus induced leukemia in mice" *J. Nat. Cancer Inst.* 26:382 (1961); Dmochowski et al. "Electron microscopic studies of rat leukemia induced with mouse leukemia virus" *Proc. Soc. Exp. Biol. Med.* 110:504–508 (1962), the disclosures of which are hereby incorporated by reference) and is specific with regard to age, strain and species that are susceptible to infection. Both MuLV and HIV belong to the group of (−) RNA viruses known as retroviruses which replicate through a DNA intermediate.

Since HIV is believed to be the causative agent of AIDS, arresting its replication has been the focus of much research. Current approved anti-HIV drugs AZT, ddI, and ddC serve as inhibitor and/or chain terminators of the RT reaction (Furman et al. "Phosphorylation of 3'-azido-3'-deoxythymidine and selective interaction of the 5'-triphosphate with Human Immunodeficiency Virus Reverse Transcriptase" *Proc. Natl. Acad. Sci. (USA)* 83:8333–8337 (1986); St. Clair et al. "3'-azido-3'-deoxythymidine triphosphate as an inhibitor and substrate of purified Human Immunodeficiency Virus Reverse Transcriptase" *Antimicrobial Agents and Chemotherapy* 31:1972–1977 (1987); Huang et al. "Selective action of 3'-azido-3'-deoxythymidine-5'-triphosphate on viral reverse transcriptases and human DNA polymerases" *J. Biol. Chem.* 265:11914–11918 (1990), the disclosures of which are hereby incorporated by reference). However, the virus is able to mutate in such a way that it is able to elude these drugs.

DNP-poly [A] was previously found to be an effective inhibitor of the reverse transcriptases from HIV-1, HIV-2, AZT and Nevirapine resistant strains of HIV as well as from MuLV in subnanomolar range in vitro (Kang, I and Wang, J. H. "Design of Structure-based Reverse Transcriptase Inhibitors" *J. Biol. Chem.* 269:12024–12031 (1994), the disclosure of which is hereby incorporated by reference). It is of great interest to find out the effect, if any, of this molecule on the progression of retroviral disease induced by the retrovirus. Below, the inhibitory effects of DNP-poly [A] and DNP derivatized antisense oligonucleotides on murine leukemia virus and on the MuLV-induced disease in Balb/c mice are described.

EXAMPLE I

Treatment of MuLV in a Mammal with DNP-Poly [A]

Previous work performed by and under the direction of the inventor has demonstrated that poly-2'-O-(2,4-dinitrophenyl) poly [A] (DNP-poly [A]) is a potent inhibitor of reverse transcriptases from a variety of sources. Kang, I and Wang, J. H. "Design of Structure-based Reverse Transcriptase Inhibitors" *J. Biol. Chem.* 269:12024–12031 (1994). In the present study, its inhibitory effect on the reverse transcriptase from Moloney Murine Leukemia Virus (MuLV RT) was investigated. DNP-poly [A] was found to enter the virus spontaneously and completely inhibit the RT within 30 minutes at 0° C. The inhibitor was also spontaneously transported into isolated human lymphocytes and leukocytes at 37° C.

Animal studies have demonstrated the effectiveness of DNP-poly [A] as an antiviral drug when administered i.p. with varying doses from 1 mg to 100 mg/kg body weight. MuLV-infected mice show the presence of RT in their blood as well as increased numbers of abnormal white blood cells. After the administration of DNP-poly [A] at a dose of 100 mg/kg body weight, three times a week over a 3 week period, RT cannot be detected by an ultrasensitive RT-PCR assay. Autopsy showed that the spleens of infected but untreated mice were enlarged 2–10 fold with fused nodules and proliferation of large abnormal lymphocytes whereas the spleens of infected but treated mice resemble the normal spleens of uninfected control mice.

As toxicity controls, uninfected mice were also injected with 1 to 100 mg DNP-poly [A]/kg body weight. They showed WBC and RBC counts within the normal range. Their spleens had normal weights and histology.

The macromolecular inhibitor poly-2'-O-(2,4-dinitrophenyl) poly[A] (DNP-poly[A]) was first designed (Kang, I and Wang, J. H. "Design of Structure-based Reverse Transcriptase Inhibitors" *J. Biol. Chem.* 269:12024–12031 (1994)) on the basis of crystallographic data on the active site of HIV RT (Kohlstaedt et al. "Crystal Structure at 3.5 Å Resolution of HIV-2 Reverse Transcriptase complexed with an inhibitor" *Science* 256:1783–1790 (1992), Arnold et al. "Structure of HIV-1 Reverse Transcriptase/DNA complex at 7 Å resolution showing active site locations" *Nature* 357: 85–89 (1992), the disclosures of which are hereby incorporated by reference) and was synthesized to investigate the inhibition of reverse transcriptases such as HIV RT (wild type) and other retroviruses. It is precisely those other retroviruses that are a focus of the present Example.

A. Materials and Methods 1.1 Compounds & Enzymes

[$^3$H] Poly [A] (22.8 Ci/mmol) was from Amersham, (Arlington Heights, Ill.) and [$^3$H] dTIP (83.8 Ci/mmol) was from NEN Du Pont, (Boston, Mass.). GF/C filters were from Whatman's (Hillsboro, Oreg.). Oxirane acrylic beads (250 µm), epoxy activated Sepharose 6B, poly [A]•[dT]$_{12}$, Ultra Pure reagents for PCR and human plasma were all from Sigma Chemical Co., (St. Louis, Mo.). RNAsin was from Promega, (Madison, Wis.), MS2 RNA from Boehringer Mannheim, (Indianapolis, Ind.), Taq DNA Polymerase and gel electrophoresis reagents were purchased from Life Technologies, (Grand Island, N.Y.). HIV RT was purchased from Worthington Biochemical Corp., (Freehold, N.J.) and stored in 10 mM potassium phosphate (pH 7.1) with 1 mM DTT and 50% glycerol (v/v) at −20° C.

1.2 Virus and Cells

M-MuLV-ecotropic (suspended in Dulbeeco's MEM (high glucose) with 10% FBS and 50 µg/ml gentamicin) and elutriated cell preparations of human lymphocytes and leukocytes were purchased from Advanced Biotechnologies, (Columbia, Md.).

1.3. Assay of RNA-dependent DNA polymerase activity of MuLV RT.

This was carried out according to the procedure of Sherr et al. "Murine Leukemia Virus Reverse Transcriptase assay" in: William B. Jakoby and Ira Pastan (Eds), *Methods in Enzymology* 58:12–417 (1979), the disclosure of which is hereby incorporated by reference in its entirety. A Beckman Airfuge was used for the high speed centrifugation step of the assay.

1.4. Testing the stability of DNP-poly [A] in 0.01M HCl at 37° C.

DNP-poly [A] was incubated in 0.01M HCL at 37° C. for 4 hrs and 24 hrs. At the end of the incubation period, each tube was immersed in liquid nitrogen to stop any further inactivation. The IC50 values of HIV RT (at 25 nM) were determined by the procedure reported elsewhere (Kang and Wang, supra (1994)). Control experiments were also run with diethylpyrocarbonate (DEPC) treated water.

1.5 Preparation of Sepharose 6B with covalently attached DNP-poly [A]

About 200 mg of epoxy-activated sepharose 6B was suspended in 4 ml of DNP-poly [A] solution (2.5 mg/ml). The suspension was mixed with 1 ml of 1.0M $K_2CO_3$ solution, adjusted to pH 10–11 with $KHCO_3$ and gently shaken for 2 days at 25° C. The derivatized resin suspension was transferred to a 3-ml syringe fitted with a filter. From the decreased absorbance of the filtrate at 259 nm, the yield was estimated to be 2 mg DNP-poly [A]/g resin. The resin was sequentially washed with water, 1.0M KCL solution and buffered medium before use.

1.6 Preparation of oxirane beads with covalently attached DNP-poly [A]

Prepared by the method of Rahman et al Anal. Chem. 68:134–138 (1996).

1.7 Binding of murine leukemia virus to DNP-poly [A] covalently attached to oxirane acrylic/sepharose beads.

Epoxy-activated Sepharose or oxirane acrylic beads with covalently attached DNP-poly [A] were pre-equilibrated with 1 ml of buffer/human plasma for 72 hrs at 25° C., At each titration step, a mixture of $10^8$ MuLV in 100 $\mu$l buffer or plasma was added to the resin suspension and shaken at 0° C. for 60 minutes. An aliquot (50 $\mu$l) of the supernatant was then removed, airfuged through a glycerol layer (20% glyceroL, 0.05M Tris-HCL pH 7.8, 0.1M KCL) at 100,000×g to pellet the virus and assayed for RT activity as described in Section 1.3.

1.8 Transport of DNP-poly [A] into murine leukemia virus.

Five $\mu$l of medium containing $6\times10^8$ v.p. was incubated at 0° C. with 10 $\mu$l of a 2 $\mu$M DNP-poly [A] stock solution. At a time 't', the virus was centrifuged through a glycerol layer for 10 minutes at 100,000 ×g. The supernatant was carefully removed and the pellet was washed with 200 $\mu$l Tris-HCL buffer (50 mM, pH 7.8) and again centrifuged. The pellet was then homogenized in 12 $\mu$l of 0.5% Triton X-100 at 0° C. for 3 minutes and incubated with MuLV RT assay mixture at 37° C. for 60 minutes. The assay reaction was terminated by the addition of 3 ml, 10% TCA. The incorporated radioactive product was collected on a GF/C filter, washed and counted in a Wallac Liquid Scintillation Counter.

1.9. Transport of DNP-poly [A] into human lymphocytes-leukocytes at 37° C.

A 400 $\mu$l suspension containing $8\times10^6$ cells in 100 $\mu$l FSA, 3.2 ml RPMI 1640 and 300 $\mu$l [$^{14}$C] DNP-poly [A] (0.05 mg/ml, 3024 cpm/$\mu$g) was divided into several aliquots and incubated at 37° C. for various lengths of time. At time 't', the incubation mixture was centrifuged at 3000 ×g for 5 minutes in an Eppendorf Centrifuge and the supernatant was discarded. The pellet was carefully washed with 300 $\mu$l of PBS, centrifuged and the supernatant discarded. This washing procedure was performed three times. The homogenized pellet was then immersed in 5 ml of counting cocktail and counted in a Wallac Liquid Scintillation counter.

1.10. Animal experiments

Fifty four male Balb/c mice, approximately 3 weeks old, were purchased from Harlan Sprague Dawley, (Indianapolis, Ind.) and weighed 12–15 g prior to infection and/or treatment. Thirty mice were infected i.p. or i.v. (via tail vein) with $10^5$ to $10^8$ virus particles ($10^{8.25}$ $TCID_{50}$/ml titered in SC-1/XC infectivity assay over a 12 day period) in saline. DNP-poly [A] was administered i.p. in saline in varying doses of 1 to 100 mg/kg body weight. Blood was periodically drawn from the tail and used in PERT assay.

1.11. Sample pre-treatment for PERT (Product Enhanced RT) assay

The method of Pyra et al. "Ultrasensitive retrovirus detection by a reverse transcriptase assay based on product enhancement" *Proc. Natl. Acad. Sci. (USA)* 91:1544–1548 (1994) (the disclosure of which is hereby incorporated by reference in its entirety) was used with some modifications. Briefly, 5 $\mu$l of whole blood was collected into 5 $\mu$l EDTA (13.8% w/v)+45 $\mu$l saline and frozen at −20° C. overnight. The hemolysed blood was then centrifuged at 4000 ×g for 30 minutes at 4° C, The supernatant was removed and again centrifuged at 100,000 ×g for 30 minutes. The pellet was then homogenized in 20 $\mu$l Buffer A containing 50 mM KCL, 50% glycerol, 25 mM Tris HCL (pH 7.5), 0.25 mM EDTA, 0.5% Triton X-100 and 5 mM DTT. This suspension was kept at 0° C. for 15 minutes and 3 $\mu$l was removed and used in the PERT assay.

1.12. PERT & Product Amplification by PCR.

The procedure described by Pyra et al. supra (1994) was carried out without any modifications.

B. RESULTS

Figure 1:
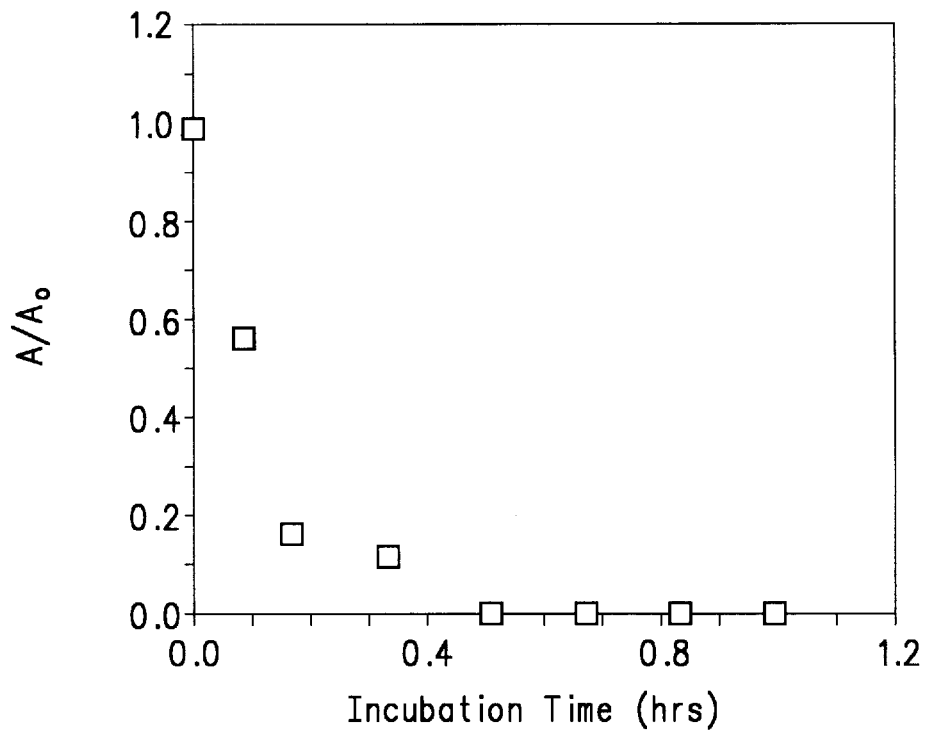
FIG. 1 is a graph showing the transport of DNP-poly [A] into MuLV virus particles and inhibition of MuLV RT at 0° C.

Intact MuLV particles in aqueous buffer exhibit no RT activity toward substrate and primer-template in external medium. But the activity can be measured by first releasing the endogenous RT with low concentrations of Triton X-100 (0.1–0.5%). In the present work, the transport of DNP-poly [A] into MuLV was monitored by mixing them in the absence of the detergent, taking aliquots of the mixture at different time intervals after mixing, centrifugation of each aliquot and washing each sediment to remove external DNP-poly [A]. The washed virus was subsequently treated with Triton X-100 to release the RT, and fmally incubated in assay solution, and the processed virus was used for determination of RT activity. The result of a typical experiment is illustrated in FIG. 1 where the observed ratio $A/A_0$ of the RT activities observed before and after incubation with DNP-poly [A] is given as a function of incubation time. It shows that even at 0° C., the macromolecule was rapidly transported into MuLV to inhibit the endogenous RT. The DNP-poly [A] used in this study has an average molecular weight of $1.1\times10^5$ and adenine/DNP molar ratio of 1.5.

Figure 2:
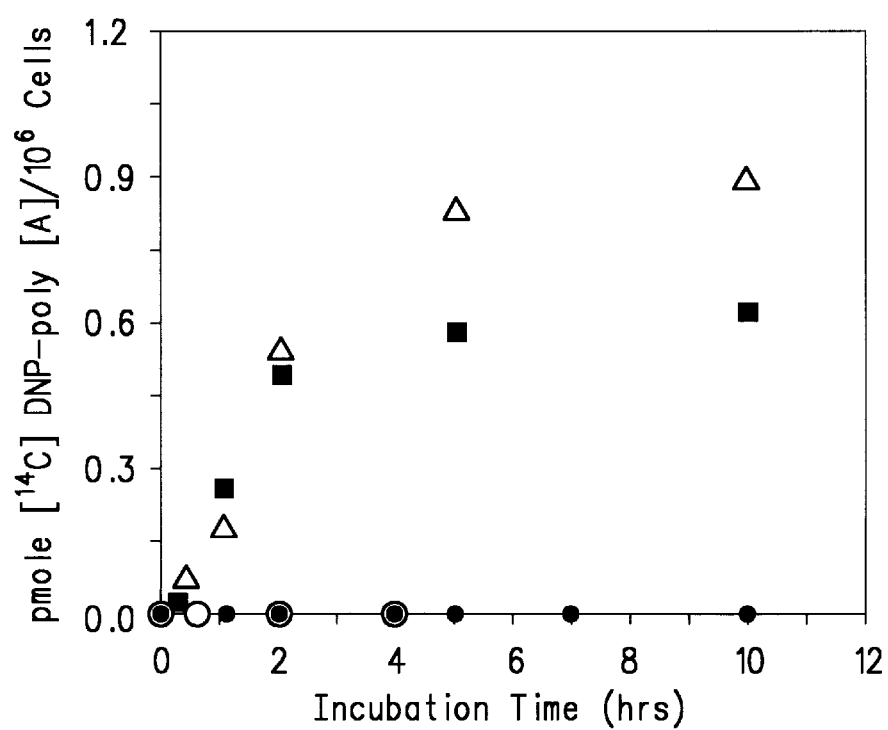
FIG. 2 is a graph showing the transport of both DNP derivatized and underivatized labeled poly [A] molecules into human cells at 37° C. as follows.

FIG. 2 illustrates similar results from experiments on the transport of DNP-[$^{14}$C] poly [A] into human lymphocytes and leukocytes, respectively, at 37° C., These observations show that the hydrophobic effect of a large number of DNP groups can compensate the hydrophilic effect of charged phosphate groups in each DNP-poly [A] molecule sufficiently to make it membrane-permeable. By contrast, the hydrophilic underivatized poly [A] of equal chain length was not at all transported under the same conditions.

To exploit this membrane-permeability, each DNP-poly [A] molecule was covalently linked to oxirane acrylic resin, and found that the resulting affinity resin can bind MULV selectively from its suspension in human plasma. Presumably, the covalently anchored DNP-poly [A] (approximately 0.06 μm in length) can penetrate into the retrovirus (approximately 0.1 μm) and catch the particles by binding to the endogenous RT as illustrated in the inset of FIG. 3. It was found that shaking with this affinity resin can selectively remove MuLV suspended in human plasma. In order to determine the binding free energy, a suspension of the affinity resin was titrated with the retrovirus. At equilibrium, the concentration of free virus (C), the moles of virus bound per mg of resin (n) and the virus binding capacity (N) are related by the equation:

$$n/C=(N-n)K_d$$

where $K_d$ is the dissociation constant of the bound virus. The corresponding linear plot of experimental data in FIG. 3 gives $K_d=3.4\times10^{-12}$ M and $N=1.4\times10^{9}$ virus particles per mg.

Unlike the natural polynucleotides, DNP-poly [A] is completely stable in solutions containing ribonucleases A, B, S, $T_1$, $T_2$, and H, as well as phosphodiesterases 1 and 2 (Rahnian et al. supra (1996)). DNP-poly [A] was also found to be quite stable in acidic medium in that it was able to retain its inhibition potency when incubated several hours in 0.01M HCL and water respectively at 37° C., FIG. 4 shows that in both situations, there is still inhibition after the incubation. The membrane permeability and chemical stability of DNP-poly [A] suggest that this RT inhibitor could be used as an unusually effective anti-retroviral agent. As a test case, MuLV-infected mice were treated with doses of DNP-poly [A] in phosphate buffered saline (D-PBS) by i.p. injection and followed their blood chemistry and spleen histology in comparison with those of the control mice (infected and untreated, uninfected and untreated, uninfected and treated, respectively).

In the early stages of the diseases, HCT measurements gave some indication on the progress of infection (FIG. 5). Mice that were treated immediately after viral infection up to 3 times, at three day intervals with 10 mg/kg body weight, did not manifest leukemic symptoms such as large splenic cells, large spleens or low hematocrit (<40%) which was observed in infected but untreated mice (FIG. 6). The subsequently treated mice had normal spleen architecture. After about 4 months, the blood from infected but untreated mice showed a strong signal on ethidium bromide stained gels obtained by PERT assay due to circulating virus particles and infected cells. This band corresponds to approximately 100 bp according to the PCR marker which was run alongside it. FIG. 7 shows that these bands progressively lost their intensity after the DNP-poly [A] treatment was introduced and continued for up to 3 weeks, and eventually disappeared. These mice, had twice the normal spleen weight at autopsy. FIG. 8 shows an infected but untreated mouse spleen (10×normal spleen weight) that is greatly enlarged and has lost the normal spleen architecture. Under high magnification, large abnormal cells can be seen to proliferate within the infected but untreated spleen to such an extent that normal lymphocytes are very rare in the whole field. Spleens of infected but treated mice had some regions of hypernodularity (FIG. 8) but there were still distinct regions of white and red pulp and their blood films looked more normal than abnormal. As toxicity controls, uninfected mice were also administered with 1 to 100 mg DNP-poly [A]. The WBC, HCT and RBC counts for these animals were within normal limits.

C. DISCUSSION

The use of macromolecular inhibitors as therapeutic agents is often hampered by their failure to cross biological transport barriers. It has now been discovered that derivatives of poly [A] with DNP groups attached to the 2'-O positions via ether linkage can be transported freely and rapidly into viruses and cells, whereas poly [A] itself cannot. This poly [A] derivative was previously shown to protect susceptible lymphocytes from HIV (Kang and Wang supra (1994)). The new transport data suggest a protection mechanism involving permeation of the inhibitor through viral and cellular membranes followed by inhibition of the reverse transcriptase inside. Although the MuLV-infected mice reported in this work were treated with DNP-poly [A] by i.p. injection, the membrane permeability and chemical stability of DNP-poly [A] suggest that oral or transdermal administration of inhibitor should also be explored.

In MuLV infected mice, more and more abnormal giant cells were observed within the spleen as the RBC population decreased eventually giving rise to anemia. The mice that were treated after 4 months of infection had obviously already developed the disease to such an extent that although viral load in blood was markedly decreased, the spleen was still infiltrated by abnormal looking cells. These large pathological cells dominated the spleen population as the disease progressed. Mice are lymphocytic animals and various investigators have documented blood lymphocyte/neutrophil ratios of ≧2. Shermer "The White Mouse" In: *The Blood Morphology of Laboratory Animals*, pp. 61–74 (1967), the disclosure of which is hereby incorporated by reference in its entirety. However, in the infected but untreated animals the ratio of lymphocyte/neutrophil was found to be <½. This observation has not been documented in MuLV infected mice. Since the mouse is an animal with very small blood volume (5.5%–8.0% body weight) multiple tests can only be performed on microscale. In the present work RT-PCR was used to monitor viral load because it requires only 5 μl of whole blood per assay.

When MuLV replicates, thereby giving rise to more virus particles, the amount of RT increases. Consequently, the cDNA produced by reverse transcription increases also. Conversely, a decrease in the intensity of the 100 bp band on ethidium bromide stained gels demonstrates a decrease in cDNA and therefore RT. The results indicate that multiple treatment with DNP-poly [A] can decrease viral load to zero. Indeed, the viral RT was still not detectable two weeks after treatment was terminated (data not shown). The PERT and RT-PCR assays developed by Pyra et al. "Ultrasensitive retrovirus detection by a reverse transcriptase assay based on product enhancement" *Proc. Natl. Acad. Sci* (USA) 91:1544–1548 (1994) (the disclosure of which is hereby incorporated by reference in its entirety) are sufficiently sensitive to detect $10^{-9}$ unit of RT activity.

MuLV RT has a molecular weight of 71,000 and a specific activity of about 40,000 units/mg and, therefore, $10^{-9}$ unit of RT would represent $2.1\times10^{2}$ RT molecules. In avian and mammalian type C retroviruses, it has been estimated that there are 20–70 RT molecules per virion. Stromberg et al. "Structural studies of Avian Myeloblastosis Virus: Comparison of polypeptides in virion and core components by dodecyl sulfite-polyacrylamide gel electrophoresis" *J. Virology* 13:513–528 (1974), the disclosure of which is hereby incorporated by reference in its entirety. This would correspond to as little as 3–11 virions detectable. Pyra et al. supra (1994). The positive controls (pure virus) gave strong signals whereas negative controls (normal uninfected blood or buffer) showed no bands. Therefore, this assay is useful and reliable for quantitation of virus load as well as determination of susceptibility of MuLV to DNP-poly [A]. One of the main problems of in vivo drug administration is the possible side effects caused by the drug. However, at the doses used in the present experiments, no toxic effects were observed. On the basis of previous in vitro studies and the present work, it seems reasonable to attribute the decrease in viral load and maintenance of normal spleen architecture to the antiretroviral activity of DNP-poly [A] although the possibility that some form of cellular immunity may have been activated during the course of treatment cannot be excluded as a possible explanation.

EXAMPLE II

Design of Antisense Oligonucleotide to Murine Leukemia Virus (MuLV)

The complete sequence of Murine Leukemia Virus has been published by Shinnick et al. *Nature* 293:543–548 (1981). The gene is 8333 bases in length. A portion of the sequence, from base 7658 to base 7672, corresponding to a polypeptide segment in the env protein that is essential for the replication of MuLV was selected. Granowitz et al. showed that mutants with altered sequence in this region of the env gene are replication-defective. Granowitz et al. *Virology* 183:545 (1991). The selected sequence is as follows:

5' GGACCCTGCATTCTT 3' (SEQ ID NO:1).

A 15-mer antisense oligonucleotide was designed to block the synthesis of MuLV. The oligoribonucleotide has the following sequence:

5' AAGAAUGCAGGGUCC 3' (SEQ ID NO:2).

The antisense oligoribonucleotide was ordered from, and custom synthesized by, Oligo Therapeutics, Inc.

EXAMPLE III

Preparation Of DNP-derivatized Antisense Oligonucleotide

In order to derivatize the antisense oligonucleotide from Example II, the oligoribonucleotide of SEQ ID NO:2 was reacted with 1-fluoro-2,4-dinitrobenzene as follows:

2 mg of SEQ ID NO:2 was dissolved in 0.1 ml of diethylpyrocarbonate (DEPC) treated water and 20 μl of 0.1M $K_2CO_3$+2.0M $KHCO_3$ buffer (pH 8.8). 3.5 μl of 1-fluoro-2,4-dinitrobenzene (FDNB) in 60 μl of acetone was mixed in. The mixture was gently stirred in a capped glass vial at 35° C. for 48 hours. As the reaction progressed, additional FDNB and $K_2CO_3$ or $KHCO_3$ were added from time to time to replenish the reagent and maintain the pH at approximately 8.8 as follows:

| Elapsed Time | FDNB added | pH | Temperature |
|---|---|---|---|
| Start | 3.5 μl | 8.8 | 35° C. |
| 1 Hour | 3.5 μl | 8.7 | 35° C. |
| 2.5 Hours | 3.5 μl | 9.1 | 35° C. |
| 5 Hours | 7 μl | 9.3 -> 8.8 | 35° C. |
| 9 Hours | 3.5 μl | 9.1 | 35° C. |
| 20 Hours | 3.5 μl | 8.3 -> 8.7 | 35° C. |
| 24 Hours | 3.5 μl | 8.6 | 35° C. |
| 29 Hours | — | — | 25° C. |
| 48 hours | reaction terminated | | |

-continued

The reaction mixture was extracted with pH 8.8 buffer plus half its volume acetone. The extract was dialyzed against water through a membrane permeable to molecules with an $M_r$<1000. The dialyzed sample was recovered and its UV absorbance at 259 and 330 was measured to determine the molar ratio of DNP to nucleotide. The absorbances, $A_{259}$=0.151 and $A_{330}$=0.023, yielded a molar ratio of 0.81 DNP to nucleotide. The overall yield of the reaction was calculated to be 72%.

EXAMPLE IV

Antisense Treatment of MuLV in a Mammal

In order to test the effectiveness of the DNP derivatized antisense oligonucleotide (SEQ ID NO:2) prepared in Example II, six Balb/c mice (all male litter mates at 3–6 weeks of age) were infected with MuLV (mice A, B, C, D, E, and F). To this end, the mice received 8.3×10⁶ VP/mouse via intravenous injection. Approximately five days later, blood samples were withdrawn from all six mice and from a normal, uninfected mouse (G) as a control. An RT-PCR assay was performed on the blood samples to determine the presence of virus. None of the seven samples exhibited virus based on electrophoresis.

On day twenty, blood samples were again withdrawn from all six mice and the samples tested for the presence of virus through RT-PCR. Three of the mice showed evidence of the virus (A, B, and F), while three others did not (C, D, and E). See FIG. 9a. On day twenty-four, two of the mice evidencing infection (A and B) were treated for a week with the antisense DNP-oligo with a dosage of 2.5 mg/kg, three times/week by intraperitoneal injection. The control mouse G that was not infected with the virus was also treated. Mouse F, which showed evidence of virus on day 20 was left untreated, as were mice C, D, and E.

Blood samples were again withdrawn from all of the mice on day thirty. Evidence of virus through RT-PCR assay and electrophoresis disappeared in the infected/treated mice (A and B). Mouse G is also free from evidence of virus. However, mice C, D, and E indicate presence of the virus. See FIG. 9b.

Treatment of mice A, B, and G was continued for an additional seven days. On day thirty-seven, blood samples were again withdrawn from all of the mice. Mice A, B, and G remained free of virus and mice C, D, and E continued to express the viral gene. See FIG. 9c.

On day forty, the treatment of mouse B was discontinued while the treatment of mice A and G was continued on a reduced dosing schedule (2.5 mg/kg, two times/week). On day 49, blood samples were withdrawn from all of the mice. Mice A, B, and G remained free from virus while mice C, D, and E continued to express the viral gene. See FIG. 9d.

The results of the experiment are summarized in the following Table.

TABLE

| Mouse | Day 1 | Day 5 RT-PCR for Virus | Day 20 RT-PCR for Virus[2] | Day 24 Treatment | Treatment | Day 30 | | Day 37 | | Day 40 Treatment | Treatment | Day 49 |
|---|---|---|---|---|---|---|---|---|---|---|---|---|
| | | | | | | RT-PCR for Virus[3] | Treatment | RT-PCR for Virus[4] | | | | RT-PCR for Virus[5] |
| A | Inoculated[1] | – | + | 2.5 mg/kg, 3X/week | 2.5 mg/kg, 3X/week | – | 2.5 mg/kg, 3X/week | – | NT | NT | – |
| B | Inoculated[1] | – | + | 2.5 mg/kg, 3X/week | 2.5 mg/kg, 3X/week | – | 2.5 mg/kg, 3X/week | – | 2.5 mg/kg, 2X/week | 2.5 mg/kg, 2X/week | – |
| C | Inoculated[1] | – | – | NT | NT | + | NT | + | NT | NT | + |
| D | Inoculated[1] | – | – | NT | NT | + | NT | + | NT | NT | + |
| E | Inoculated[1] | – | – | NT | NT | + | NT | + | NT | NT | + |
| F | Inoculated[1] | – | + | NT | NT | + | NT | + | NT | NT | + |
| G | Control | – | – | 2.5 mg/kg, 3X/week | 2.5 mg/kg, 3X/week | – | 2.5 mg/kg, 3X/week | – | 2.5 mg/kg, 2X/week | 2.5 mg/kg, 2X/week | – |

NT = Not treated.
Note 1 = Inoculation was accomplished with 8.3 × 10^6 virus particles per mouse.
Note 2 = See FIG. 9a.
Note 3 = See FIG. 9b.
Note 4 = See FIG. 9c.
Note 5 = See FIG. 9d.

The above data indicates that the antisense DNP oligonucleotides of the present invention operate to block synthesis of the viral envelope protein of MuLV. The nucleotides appeared to have been freely available to infected cells. This finding is supported by the results presented in Example I relating to the bioavailability of DNP-poly [A]. Moreover, the nucleotides did not appear to be susceptible to enzymatic degradation. This finding is again supported by the results demonstrated in Example I related to the enzymatic degradation of DNP-poly [A]. Particularly impressive with respect to the data was the fact that upon discontinuing treatment in mouse B there was no evidence of viral infection persisting. This fact appears to demonstrate that either the oligonucleotide persisted in hybridizing to the MuLV gene or that the MuLV infection was vanquished by the host mouse.

EXAMPLE V

Design of Antisense Oligonucleotide to Duck Hepatitis B Virus (HBV)

The complete sequence of Duck Hepatitis B Virus has been published by Schneider et al. in GenBank, Title: GBVRL2.SEQ, Locus: DHVBCG, Accession: X60213 (19–11–1992). The gene is 3027 bases in length. A portion of the sequence, from base 798 to base 813, at the initiation site of the pre-S gene was selected. Offensberger et al. showed that the phophorothioate modified antisense corresponding to bases 795 through 812 inhibited the replication of HBV in ducks (DHBV). Offensberger et al. *EMBOJ* 12:1257–1262 (1993). The selected sequence is as follows:

5' CTGATGGGACAACAA 3' (SEQ ID NO:3).

A 15-mer antisense oligonucleotide is designed to block the synthesis of HBV. The oligoribonucleotide has the following sequence:

5' UUGUUGUCCCAUCAG 3' (SEQ ID NO:4).

The antisense oligoribonucleotide is ordered from, and custom synthesized by, Oligo Therapeutics, Inc.

EXAMPLE VI

Preparation Of DNP-derivatized Antisense Oligonucleotide

In order to derivatize the antisense oligonucleotide from Example V, the oligoribonucleotide of SEQ ID NO:4 is reacted with 1-fluoro-2,4-dinitrobenzene as described in Example II.

EXAMPLE VII

Antisense Treatment of Duck (Avian) HBV

Approximately 25% to 30% of all ducklings are naturally infected with HBV. Ducks testing positive for HBV by RT-PCR and ducks testing negative for HBV will be used to test the effectiveness of the antisense therapy. Ducks can be obtained from Metzer Farms, Gonzales, Calif. A similar experimental design is used as was used in Example IV.

It is expected that ducks testing positive for HBV that are not treated with the derivatized antisense oligonucleotide of SEQ ID NO:4 will continue to be infected and will die while ducks testing positive for HBV that are treated with the derivatized antisense oligonucleotide of SEQ ID NO:4 will cease to be infected and will thrive. Further, ducks that are not infected with HBV that are treated with the derivatized antisense oligonucleotide of SEQ ID NO:4 will continue to be healthy and thrive.

In accordance with Offensberger et al. *EMBOJ* 12:1257–1262 (1993), infected ducklings were treated with daily intrvenous injections of the phosphorothioate modified antisense DNA and the effective dosage was found to be 20 mg/kg. It is expected that the effective concentration of the present antisense oligonucleotides will be much lower than Offensberger et al. because of the enhanced membrane permeability and stability of nucleotides derivatized in accordance with the invention. In the present experiment, dosing will be started at 0.2 mg/kg and will be scaled up in the range of 0.2 mg/kg to less than about 20 mg/kg to determine efficacy. It is expected that efficacy will be apparent in the range of about 1 mg/kg to about 10 mg/kg and may well be apparent in the same range as that observed for MuLV above of 2.5 mg/kg.

EXAMPLE VIII

Preparation of Derivatized Oligonucleotides

Antisense and sense phosphorothioate oligonucleotides can be readily prepared on 1 μmol or 10 μmol scales with an Applied Biosystems Model 380B DNA synthesizer using reported procedures in Zon et al. *Oligonucleotides and Analogues: A Practical Approach*, F. Eckstein, Ed. (Oxford University Press, Oxford, England), pp. 87–108 (1991), the disclosure of which is hereby incorporated by reference. The process generally includes substitution of a sulfur-donor reagent (as described in U.S. Pat. No. 5,151,510, the disclosure of which is hereby incorporated by reference) for iodine-water-pyridine, reversing the normal oxidation-then-cap sequence within each cycle, preparative reversed-phase high-performance liquid chromatography, detritylation, isolation of the final product in the form of its sodium salt, and then analysis by capillary gel electrophoresis. See also Zon et al. *Anti-Cancer Drug Design* 6:539 (1991), the disclosure of which is hereby incorporated by reference. Product is generally recovered as greater than or equal to 85 percent of full-length product through comparison to size standards. Antisense therapy is a young art, however, some of the first antisense therapeutic agents have gone into human patients in the last several years. E.g., Bayever et al. *Antisense Research and Development* 2:109–110 (1992). It is expected, therefore, that the antisense oligomers of the present invention can be suitably used in vivo in humans.

Accordingly, it is believed that antisense therapies in accordance with the invention provides a highly efficacious form of therapy.

As will be understood, in order to effectively treat diseases with the antisense oligomers of the present invention, it is necessary that the oligomers are able to gain access to the afflicted area. Moreover, it will be appreciated that any of the antisense oligomers prepared in accordance with the present invention that show antiproliferative effect can be used in treatment.

It is expected that direct injection into lesions and intravenous administration of the antisense oligomers of the present invention are currently the most efficient and expedient forms of delivery. However, it is also anticipated that a variety of topical formulations will show similar efficacy. Intravenous administration is generally indicated in advanced cases of non-localized diseases.

The antisense oligomers of the present invention can be formulated into a medicament to aid in stabilizing and/or aiding their delivery to the afflicted site. A multitude of appropriate formulations can be found in the formulary known to all pharmaceutical chemists: Remington's Pharmaceutical Sciences, 15th Edition, 1975. Mack Publishing Company, Easton, Pa. 18042. (Chapter 87: Blaug, Seymour).

For direct injection or in intravenous administration of antisense oligomers it is conventional to include in the formulations physiologically acceptable buffers, excipients, and/or other delivery agents. For topical use, appropriate formulations include for example, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. Topical application may be highly effective. For example, certain investigators have demonstrated that certain antisense oligomers are readily absorbed by the skin. In particular, these researcher used methylphosphonates. Uhlmann et al. *Chemical Reviews* 90:543–584 at p. 568 (1990).

Moreover, liposomes have shown great promise in assisting in the delivery of oligomers, in general, and antisense oligomers in particular. One highly advantageous example of a suitable liposomal delivery vehicle is prepared from cationic lipids, such as those available under the trademark LIPOFECTIN (Life Technologies, Inc., Bethesda, Md.).

The concentration or dose of the antisense oligomers of the present invention should range from 0.1 $\mu$M through 20 $\mu$M, depending on the seriousness of the affliction, or more preferably from 0.5 $\mu$M to 5 $\mu$M. The dosage will also depend on the type of oligonucleotide and also upon its chemical modification, if any. As will be understood, the schedule of the administration will also depend on the type of oligomers used and their chemical modification, since different chemical modification effects the half-life of these compounds.

INCORPORATION BY REFERENCE

A variety of references are cited herein. Some of such references have been expressly incorporated by reference. To the extent that any reference cited herein is not expressly incorporated by reference above, the disclosures of each of such references are hereby incorporated by reference in their entirety.

EQUIVALENTS

While the present invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and any equivalents thereof.

What is claimed is:

1. An antisense oligoribonucleotide conjugated at the 2'-O position with a substituted phenyl group to produce a derivatized compound of the following general structure:

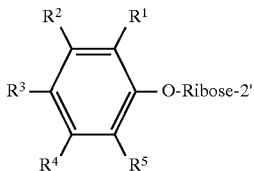

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphorothioate, or phosphothioate.

2. The oligoribonucleotide of claim 1, wherein $R^1$ and $R^3$ are $NO_2$ as follows:

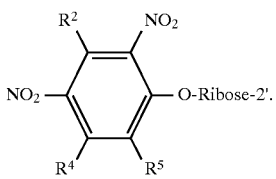

3. The oligoribonucleotide of claim 2, wherein $R^2$, $R^4$, and $R^5$ are H.

4. The oligoribonucleotide of claim 1, wherein the oligoribonucleotide has a length of between 10 and 40 nucleotides.

5. The oligoribonucleotide of claim 1, wherein the oligoribonucleotide has a length of between 12 and 30 nucleotides.

6. The oligoribonucleotide of claim 1, wherein the oligoribonucleotide has a length of between 15 and 25 nucleotides.

7. The oligoribonucleotide of claim 2, wherein the oligoribonucleotide has a length of between 10 and 40 nucleotides.

8. The oligoribonucleotide of claim 2, wherein the oligoribonucleotide has a length of between 12 and 30 nucleotides.

9. The oligoribonucleotide of claim 2, wherein the oligoribonucleotide has a length of between 15 and 25 nucleotides.

10. The oligoribonucleotide of claim 3, wherein the oligoribonucleotide has a length of between 10 and 40 nucleotides.

11. The oligoribonucleotide of claim 3, wherein the oligoribonucleotide has a length of between 12 and 30 nucleotides.

12. The oligoribonucleotide of claim 3, wherein the oligoribonucleotide has a length of between 15 and 25 nucleotides.

13. The antisense oligoribonucleotide of claim 1, wherein at least one of the 5'-OH and 3'-OH ends of the oligoribonucleotide is conjugated with a substituted phenyl group at a 2'-O ribose position to produce a derivatized compound of the following general structure:

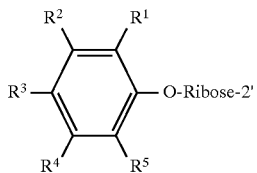

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphorothioate, or phosphothioate.

14. The oligoribonucleotide of claim 13, wherein $R^1$ and $R^3$ are $NO_2$.

15. The oligoribonucleotide of claim 14, wherein $R^2$, $R^4$, and $R^5$ are H.

16. An antisense oligoribonucleotide derivatized at a plurality of 2'-O positions with a hydrophobic group selected from the group consisting of a 2,4-dinitrophenyl group and a 3-fluoro-4,6-dinitrophenyl group.

17. The oligoribonucleotide of claim 16, wherein the oligoribonucleotide has a length of between 10 and 40 nucleotides.

18. The oligoribonucleotide of claim 16, wherein the oligoribonucleotide has a length of between 12 and 30 nucleotides.

19. The oligoribonucleotide of claim 16, wherein the oligoribonucleotide has a length of between 15 and 25 nucleotides.

20. A method of enhancing membrane permeability and stability of an oligoribonucleotide, comprising:
providing an oligoribonucleotide having a plurality of 2'-O positions;
conjugating a substituted phenyl group at said plurality of 2'-O ribose positions to produce a derivatized compound of the following general structure:

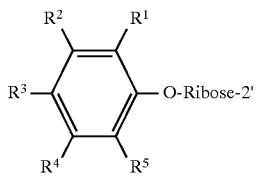

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphorothioate, or phosphorothioate.

21. The method claim 20, wherein $R^1$ and $R^3$ are $NO_2$ as follows:

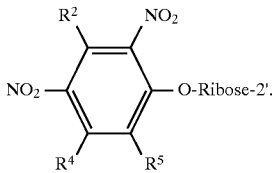

22. The method claim 21, wherein $R^2$, $R^4$, and $R^5$ are H.

23. The method of claim 20, wherein the oligoribonucleotide has a length of between 10 and 40 nucleotides.

24. The method of claim 20, wherein the oligoribonucleotide has a length of between 12 and 30 nucleotides.

25. The method of claim 20, wherein the oligoribonucleotide has a length of between 15 and 25 nucleotides.

26. The method of claim 21, wherein the oligoribonucleotide has a length of between 10 and 40 nucleotides.

27. The method of claim 21, wherein the oligoribonucleotide has a length of between 12 and 30 nucleotides.

28. The method of claim 21, wherein the oligoribonucleotide has a length of between 15 and 25 nucleotides.

29. The method of claim 22, wherein the oligoribonucleotide has a length of between 10 and 40 nucleotides.

30. The method of claim 22, wherein the oligoribonucleotide has a length of between 12 and 30 nucleotides.

31. The method of claim 22, wherein the oligoribonucleotide has a length of between 15 and 25 nucleotides.

32. The method of claim 20, wherein at least one of the 5'-OH and 3'-OH ends of the oligoribonucleotide is conjugated with a substituted phenyl group at a 2'-O ribose position to produce a derivatized compound of the following general structure:

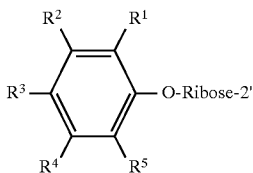

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphorothioate, or phosphorothioate.

33. The method of claim 32, wherein $R^1$ and $R^3$ are $NO_2$.

34. The method of claim 33, wherein $R^2$, $R^4$, and $R^5$ are H.

35. In an antisense therapeutic method, comprising administering an antisense oligonucleotide comprising a plurality of 2'-O positions in a manner designed inhibit gene expression, the improvement comprising:

derivatizing the antisense oligonucleotide at a plurality of the 2'-O positions with a substituted phenyl group to produce a derivatized compound of the following structure:

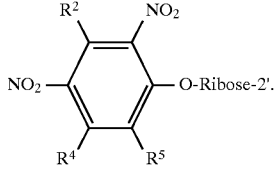

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphorothioate.

36. In the improvement of claim 35, wherein $R^1$ and $R^3$ are $NO_2$ as follows:

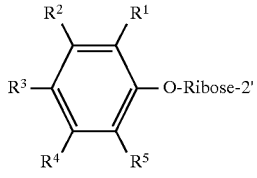

37. In the improvement of claim 36, wherein $R^2$, $R^4$, and $R^5$ are H.

38. In the improvement of claim 35, wherein the oligoribonucleotide has a length of between 10 and 40 nucleotides.

39. In the improvement of claim 35, wherein the oligoribonucleotide has a length of between 12 and 30 nucleotides.

40. In the improvement of claim 35, wherein the oligoribonucleotide has a length of between 15 and 25 nucleotides.

41. In the improvement of claim 36, wherein the oligoribonucleotide has a length of between 10 and 40 nucleotides.

42. In the improvement of claim 36, wherein the oligoribonucleotide has a length of between 12 and 30 nucleotides.

43. In the improvement of claim 36, wherein the oligoribonucleotide has a length of between 15 and 25 nucleotides.

44. In the improvement of claim 37, wherein the oligoribonucleotide has a length of between 10 and 40 nucleotides.

45. In the improvement of claim 37, wherein the oligoribonucleotide has a length of between 12 and 30 nucleotides.

46. In the improvement of claim 37, wherein the oligoribonucleotide has a length of between 15 and 25 nucleotides.

47. In the improvement of claim 35, wherein at least one of the 5'-OH and 3'-OH ends of the oligoribonucleotide is conjugated to a substituted phenyl group at a 2'-O ribose position to produce a derivatized with a compound of the following general structure:

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphorothioate.

48. In the improvement of claim 47, wherein $R^1$ and $R^3$ are $NO_2$.

49. In the improvement of claim 48, wherein $R^2$, $R^4$, and $R^5$ are H.

50. In a method for administering an oligoribonucleotide, wherein the oligoribonucleotide comprises a plurality of 2'-O positions in a manner designed to inhibit gene expression the improvement comprising:

derivatizing the O at a plurality of the 2'-O positions with a moiety selected from the group consisting of a 2,4-dinitrophenyl moiety and a 3-fluoro-4,6-dinitrophenyl moiety.

51. In the improvement of claim 50, wherein the oligoribonucleotide has a length of between 10 and 40 nucleotides.

52. In the improvement of claim 50, wherein the oligoribonucleotide has a length of between 12 and 30 nucleotides.

53. In the improvement of claim 50, wherein the oligoribonucleotide has a length of between 15 and 25 nucleotides.

54. In the improvement of claim 50, wherein at least one of the 5'-OH and 3'-OH ends of the oligoribonucleotide is conjugated with a substituted phenyl group at a 2'-O ribose position to produce a derivatized compound of the following general structure:

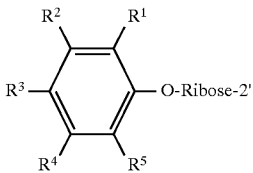

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphorothioate, or phosphorothioate.

55. In the improvement of claim 50, wherein $R^1$ and $R^3$ are $NO_2$.

56. In the improvement of claim 50, wherein $R^2$, $R^4$, and $R^5$ are H.

57. The oligonucleotide of any of claims 1–56, wherein the oligonucleotide is an antisense oligonucleotide.

58. A method of derivatizing an oligoribonucleotide, comprising:

providing an oligoribonucleotide having a plurality of 2'-O positions;

conjugating a substituted phenyl group at a plurality of 2'-O positions to produce a derivatized compound of the following general structure:

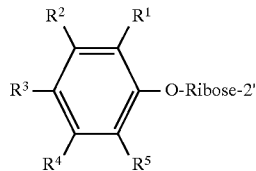

wherein $R^1$, $R^2$, $R^3$, $R^4$, and $R^5$ are independently H, $NO_2$, halide, linear or branched alkyl, linear or branched acyl, linear or branched alkylene, linear or branched O-alkyl, linear or branched amido, linear or branched S-alkyl, mono or disubstituted amine, linear or branched thioamido, phosphothionate, or phosphorothioate.

59. The method of claim 58, wherein $R^1$ and $R^3$ are $NO_2$.

60. The method of claim 58, wherein $R^2$, $R^4$, and $R^5$ are H.

61. A method of derivatizing an oligoribonucleotide, comprising:

providing an oligoribonucleotide having a plurality of 2'-O positions;

reacting said oligoribonucleotide with a Sanger-type reagent at a plurality of 2'-O positions to produce a derivatized oligoribonucleotide of the following general structure:

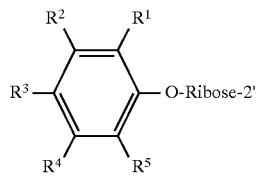

62. The method of claim 61, wherein $R^1$ and $R^3$ are $NO_2$.

63. The method of claim 61, wherein $R^2$, $R^4$, and $R^5$ are H.

* * * * *

UNITED STATES PATENT AND TRADEMARK OFFICE
CERTIFICATE OF CORRECTION

PATENT NO. : 5,858,988
DATED : January 12, 1999
INVENTOR(S) : Wang

It is certified that error appears in the above-identified patent and that said Letters Patent is hereby corrected as shown below:

In The Title Page
[76]: Cancel "5500 N. Bailey Ave." and insert --47 Le Brun Road--;
[*]: Cancel "Pat. No. 5,459,646" and insert --Pat. No. 5,496,546--

In The Specification
Col. 24, line 52: Cancel "thirty-seven" and insert --thirty-eight--
line 59: Cancel "day 49" and insert --day 50--.

Col. 26, Table Heading: Cancel "Day 37" and insert --Day 38--;
Table Heading: Cancel "Day 49" and insert --Day 50--.

In The Claims
Col. 31, line 18: Cancel "phosphorothioate" and insert --phosphothionate--
Col. 32, line 18: Cancel "phosphorothioate" and insert --phosphothionate--; line 24: Delete "antisense"
Col. 33, line 54: Cancel "phosphorothioate, or phosphorothioate" and insert --phosphothionate, or phosphothioate--
Col. 34, line 15: Cancel "phosphorothioate" and insert --phosphothioate--; line 67: Cancel "phosphorothioate" and insert --phosphothioate--
Col. 35, line 38: Cancel "phosphorothioate" and insert --phosphothioate--
Col. 36, line 21: Cancel "phosphorothioate" and insert --phosphothioate--

UNITED STATES PATENT AND TRADEMARK OFFICE
CERTIFICATE OF CORRECTION

PATENT NO. : 5,858,988
DATED : January 12, 1999
INVENTOR(S) : Wang

It is certified that error appears in the above-identified patent and that said Letters Patent is hereby corrected as shown below:

Col. 21, line 15: Cancel "n/c=(N-n)Kd" and insert --n/c=(N-n)/Kd--; Col. 31, lines 2 and 61: Delete the word "antisense"; Col. 33, lines 59-62: Cancel "In an antisense therapeutic method, comprising administering an antisense oligonucleotide comprising" and insert -- In a method for administering an oligonucleotide, wherein the oligonucleotide comprises --

Signed and Sealed this

Twenty-third Day of May, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO (v) FRAGMENT TYPE:

(vi) ORIGINAL SOURCE:

(xi) SEQUENCE DESCRIPTION: SEQ ID NO:1:

GGACCCTGCA TTCTT                                                                                               15

(2) INFORMATION FOR SEQ ID NO:2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

AAGAAUGCAG GGUCC                                                                                               15

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CTGATGGGAC AACAA                                                                                               15

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

UUGUUGUCCC AUCAG                                                                                               15